US008034928B2

(12) United States Patent
Raines et al.

(10) Patent No.: US 8,034,928 B2
(45) Date of Patent: Oct. 11, 2011

(54) FLUORESCENCE ASSAYS WITH IMPROVED SENSITIVITY

(75) Inventors: Ronald T. Raines, Madison, WI (US); Sunil S. Chandran, Fremont, CA (US); Timothy E. Glass, Columbia, MO (US); Luke D. Lavis, Madison, WI (US)

(73) Assignees: Wisconsin Alumni Research Foundation, Madison, WI (US); The Penn State Research Foundation, Univeristy Park, PA (US)

( * ) Notice: Subject to any disclaimer, the term of this patent is extended or adjusted under 35 U.S.C. 154(b) by 128 days.

(21) Appl. No.: 12/426,997

(22) Filed: Apr. 21, 2009

(65) Prior Publication Data

US 2009/0299061 A1    Dec. 3, 2009

Related U.S. Application Data

(63) Continuation of application No. 10/988,979, filed on Nov. 15, 2004, now Pat. No. 7,534,902.

(60) Provisional application No. 60/520,464, filed on Nov. 14, 2003.

(51) Int. Cl.
  C07D 407/00   (2006.01)
  C07D 493/00   (2006.01)
  C07D 273/00   (2006.01)

(52) U.S. Cl. .......................... 544/70; 549/265

(58) Field of Classification Search .......... 549/265; 544/70
  See application file for complete search history.

(56) References Cited

U.S. PATENT DOCUMENTS

| | | | |
|---|---|---|---|
| 4,714,763 A | 12/1987 | Theodoropulos | |
| 5,112,739 A | 5/1992 | Meneghini et al. | |
| 5,672,584 A | 9/1997 | Borchardt et al. | |
| 5,965,119 A | 10/1999 | Greenwald et al. | |
| 6,030,997 A | 2/2000 | Eilat et al. | |
| 6,162,931 A | 12/2000 | Gee et al. | |
| 6,214,330 B1 | 4/2001 | Greenwald et al. | |
| 6,303,569 B1 | 10/2001 | Greenwald et al. | |
| 6,335,429 B1 | 1/2002 | Cai et al. | |
| 6,413,507 B1 | 7/2002 | Bentley et al. | |
| 6,461,602 B2 | 10/2002 | Bentley et al. | |
| 6,514,491 B1 | 2/2003 | Bentley et al. | |
| 6,570,040 B2 | 5/2003 | Saxon et al. | |
| 7,534,902 B2 * | 5/2009 | Raines et al. | 549/223 |
| 2002/0006898 A1 | 1/2002 | Greenwald et al. | |

FOREIGN PATENT DOCUMENTS

| | | |
|---|---|---|
| WO | WO 99/18856 | 4/1999 |
| WO | WO 03/062451 | 7/2003 |
| WO | WO 03/099780 | 12/2003 |

OTHER PUBLICATIONS

Achilles, K., Coumarin derivatives as protease-sensitive prodrugs, Arch. Pharm. Pharm. Med. Chem. 334:209-215, 2001.
Amsberry, K. L. et al., Amine prodrugs which utilize hydroxyl amide lactonization. I. A potential redox-sensitive amide prodrug, Pharm. Res. 8(3):323-330, 1991.
Amsberry, K. L. et al., Amine prodrugs which utilize hydroxyl amide lactonization. II. A potential esterase-sensitive amide prodrug, Pharm. Res. 8(4):455-461, 1991.
Borchardt, R. T. et al., Stereopopulation control. II. Rate enhancement of intramolecular nucleophilic displacement, J. Am. Chem. Soc. 94(26):9166-9174, 1972.
Chandran, S. S. et al., Latent fluorophore based on the trimethyl lock, J. Am. Chem. Soc. 127:1652-1653, 2005.
Danforth, C. et al., Steric acceleration of lactonization reactions: An analysis of "stereopopulation control," J. Am. Chem. Soc. 98(14):4275-4281, 1976.
Dillon, M. P. et al., Application of the "trimethyl lock" to Ganciclovir, a pro-prodrug with increased oral bioavailability, Bioorg. Med. Chem. Lett. 6(14):1653-1656, 1996.
Fickling, M. M. et al., Hammett substituent constants for electron-withdrawing substituents: Dissociation of phenols, anilinium ions and dimethylanilinium ions, J. Am. Chem. Soc. 81:4226-4230, 1959.
Goldberg, J. M. et al., Kinetic mechanism of a partial folding reaction. 1. Properties of the reaction and effects of denaturants, Biochemistry 37:2546-2555, 1998.
Greenwald, R. B. et al., Drug delivery systems based on trimethyl lock lactonization: Poly(ethylene glycol) prodrugs of amino-containing compounds, J. Med. Chem. 43:475-487, 2000.
Haigis, M. C. et al., Secretory ribonucleases are internalized by a dynamin-independent endocytic pathway, J. Cell Sci. 116:313-324, 2003.
Hall, D. et al., Macromolecular crowding: Qualitative and semiquantitative successes, quantitative challenges, Biochim. Biophys. Acta 1649:127-139, 2003.
Karle, J. M. et al., Correlation of reaction rate acceleration with rotational restriction. Crystal-structure analysis of compounds with a trialkyl lock, J. Am. Chem. Soc. 94(26):9182-9189, 1972.
Karstens, T. et al., "Rhodamine B and Rhodamine 101 as reference substances for fluorescence quantum yield measurements," J. Phys. Chem. 84:1871-1872, 1980.
Leytus, S. P. et al., Rhodamine-based compounds as fluorogenic substrates for serine proteinases, Biochem. J. 209:299-307, 1983.
Milstien, S. et al., "Rate acceleration by stereopopulation control: Models for enzyme action," Proc. Natl. Acad. Sci. USA 67(3):1143-1147, Nov. 15, 1970.

(Continued)

*Primary Examiner* — D M Seaman
*Assistant Examiner* — Niloofar Rahmani
(74) *Attorney, Agent, or Firm* — Greenlee Sullivan P.C.

(57) ABSTRACT

Latent fluorescent compounds, comprising a fluorescent molecule with one or more blocking groups attached and optionally one or more urea-containing groups are provided. The urea-containing group can be used to further attach one or more molecules of interest, such as proteins, peptides or nucleic acids. The blocking group(s) is released from the latent fluorescent compound by reaction with a trigger, forming the fluorescent molecule which can be detected. Also provided herein are methods of using latent fluorescent compounds to detect triggers.

6 Claims, 6 Drawing Sheets

OTHER PUBLICATIONS

Milstien, S. et al., "Stereopopulation control. I. Rate enhancement in the lactonizations of *o*-hydroxyhydrocinnamic acids," J. Am. Chem. Soc. 94(26):9158-9165, 1972.

Nicolaou, M. G. et al., Phosphate prodrugs for amines utilizing a fast intramolecular hydroxyl amide lactonization, J. Org. Chem. 61:8636-8641, 1996.

Pauletti, G. M. et al., Esterase-sensitive cyclic prodrugs of peptides: Evaluation of a phenylpropionic acid promoiety in a model hexapeptide, Pharm. Res. 14(1):11-17, 1997.

Rotman, B. et al., Membrane properties of living mammalian cells as studied by enzymatic hydrolysis of fluorogenic esters, Proc. Natl. Acad. Sci. USA 55(1):134-141, Jan. 15, 1966.

Seglen, P. O. et al., Inhibition of the lysosomal pathway of protein degradation in isolated rat hepatocytes by ammonia, methylamine, chloroquine and leupeptin, Eur. J. Biochem. 95:215-225, 1979.

Shan, D. et al., Prodrug strategies based on intramolecular cyclization reactions, J. Pharm. Sci. 86(7):765-767, 1997.

Zhang, J. et al., Creating new fluorescent probes for cell biology, Nat. Rev. Mol. Cell Biol. 3:906-918, 2002.

Zlokarnik, G. et al., Quantitation of transcription and clonal selection of single living cells with β-lactamase as reporter, Science 279(5347):84-88, Jan. 2, 1998.

International Search Report, International Application No. PCT/US04/38183, Dec. 15, 2005, 4 pages.

* cited by examiner

FLUORESCENCE ASSAYS WITH IMPROVED SENSITIVITY

CROSS-REFERENCE TO RELATED APPLICATIONS

This application is a continuation of application Ser. No. 10/988,979, filed Nov. 15, 2004, which takes priority from U.S. provisional application 60/520,464, filed Nov. 14, 2003, hereby incorporated by reference to the extent not inconsistent with the disclosure herewith.

STATEMENT REGARDING FEDERALLY SPONSORED RESEARCH OR DEVELOPMENT

This invention was made with United States government support awarded by the following agency: National Institutes of Health CA073808 and GM044783. The United States Government has certain rights in this invention.

BACKGROUND OF THE INVENTION

Fluorescent molecules are widely used in chemistry and biochemistry. Fluorescent molecules are used to tag molecules for detection in a number of assays based on the creation or destruction of a fluorescent compound, providing a sensitive means to follow a reaction. For the most sensitive detection in a fluorescence-based system, the background signal should be small (i.e., little or no fluorescence) so there is an easily detectable signal. However, in common assays, the background fluorescence reduces the detection limit and sensitivity of the assay. An improved fluorescence assay is needed.

Prodrugs have been described which contain blocking groups which release the active drug upon activation with a suitable chemical trigger. For example, U.S. Pat. No. 6,030,997 describes a prodrug containing a pharmacologically active compound covalently bonded to a blocking group, whereby at pH 4 to 7, the covalent bond between the blocking group and pharmacologically active compound is broken, releasing the pharmacologically active compound. U.S. Pat. No. 5,672,584 describes the use in vivo of esterases which release peptides from cyclic peptide compounds. U.S. Pat. No. 5,965,119; continuation-in-part U.S. Pat. Nos. 6,303,569 and 6,214,330 describe double prodrug compounds having two cleavable groups—the first cleavable group is hydrolyzed and the second cleavable group undergoes the trialkyl lock lactonization reaction to release the desired compound. U.S. Pat. Nos. 6,413,507, 6,461,602 and 6,514,491 describe poly (ethylene glycol) compounds where a biologically active agent is linked to a poly(ethylene glycol) polymer through a hydrolyzable carbamate bond. The biologically active agent is released through hydrolysis of the carbamate bond.

PCT publication WO 03/099789 describes detection of enzymes using rhodamine derivatives substituted at one xanthylium amine group with a peptide which is protease cleavable and substituted at the other xanthylium amine group with a urea morpholine group. The bis-substituted derivative is reportedly not fluorescent. Upon exposure to the enzyme, the protease cleavable group is removed and the molecule is reported to become fluorescent. PCT publication WO 99/18856 describes detection of enzymes using rhodamine molecules substituted with specific enzyme-cleavable amino acid sequences. When contacted with an enzyme, the enzyme-cleavable amino acid sequences are removed from the rhodamine molecule and the rhodamine molecule reportedly shows an increase in fluorescence emission. PCT publication WO 03/062451 describes fluorescent compounds used to detect transport of target molecules across cell membranes. In WO 03/062451, the target molecule is linked to the fluorescent compound, making the compound non-fluorescent. The linkage between the compound and target molecule is cleaved upon entry into the cell membrane, resulting in compound fluorescence.

There is a need in the art for an improved fluorescence assay having blocking groups which release a fluorescent molecule upon activation with a trigger and optional urea-containing groups which can be used to attach desired groups to the fluorescent molecule.

BRIEF SUMMARY OF THE INVENTION

Provided herein are latent fluorescent compounds comprising a fluorescent molecule with one or more blocking groups attached and one or more optional urea-containing groups attached. The blocking group(s) are released from the latent fluorescent compound by reaction with a trigger, producing a fluorescent molecule which can be detected. The trigger can be any chemical functionality or physical change that causes the blocking group(s) to release from the latent fluorescent compound, such as an enzymatic reaction, the presence of a chemical functionality such as an azide, or a pH change. The urea-containing group(s) provide a position for attaching a desired molecule or group to the latent fluorescent compound. The desired molecule or group can be a peptide, protein or nucleic acid, for example.

Also provided are methods of detecting triggers using the latent fluorescent compounds described herein. These methods comprise providing a latent fluorescent compound containing at least one blocking group and optionally one or more urea-containing groups; and providing a trigger which selectively reacts with the latent fluorescent compound to remove the blocking group, forming a fluorescent molecule. The fluorescent molecule is then detected, indicating the presence of the trigger.

The latent fluorescent compounds of the invention are useful in assays. For example, if an enzymatic reaction is the trigger, the formation of a fluorescent signal in an appropriate detecting apparatus indicates the presence of the enzyme trigger. Also, the intensity of the fluorescence from the fluorescent molecule provides information regarding the concentration of triggers present in the system. In addition, attachment of a biological group of interest to the urea-containing group provides a method to monitor the biological group of interest in a variety of applications, as known in the art. Other applications of the invention are known and will be readily apparent to one of ordinary skill in the art in view of the disclosure provided herewith.

As used herein, "fluorescence" includes phosphorescence. As used herein, "attach" means two groups are chemically or physically joined together. "Attach" includes covalent bonds, ionic bonds, hydrogen bonds, coordinate covalent bonds and other forms of bonding or attraction known in the art. Any type of attachment of the one or more blocking groups to the fluorescent molecule is useful as long as the blocking groups are releasable from the fluorescent molecule selectively through application of a suitable trigger. Any type of attachment of the one or more urea-containing groups to the fluorescent molecule is useful as long as the urea-containing groups can be used as desired, including for attaching a desired molecule or group to the latent fluorescent compound.

DETAILED DESCRIPTION OF THE INVENTION

Figure 1:
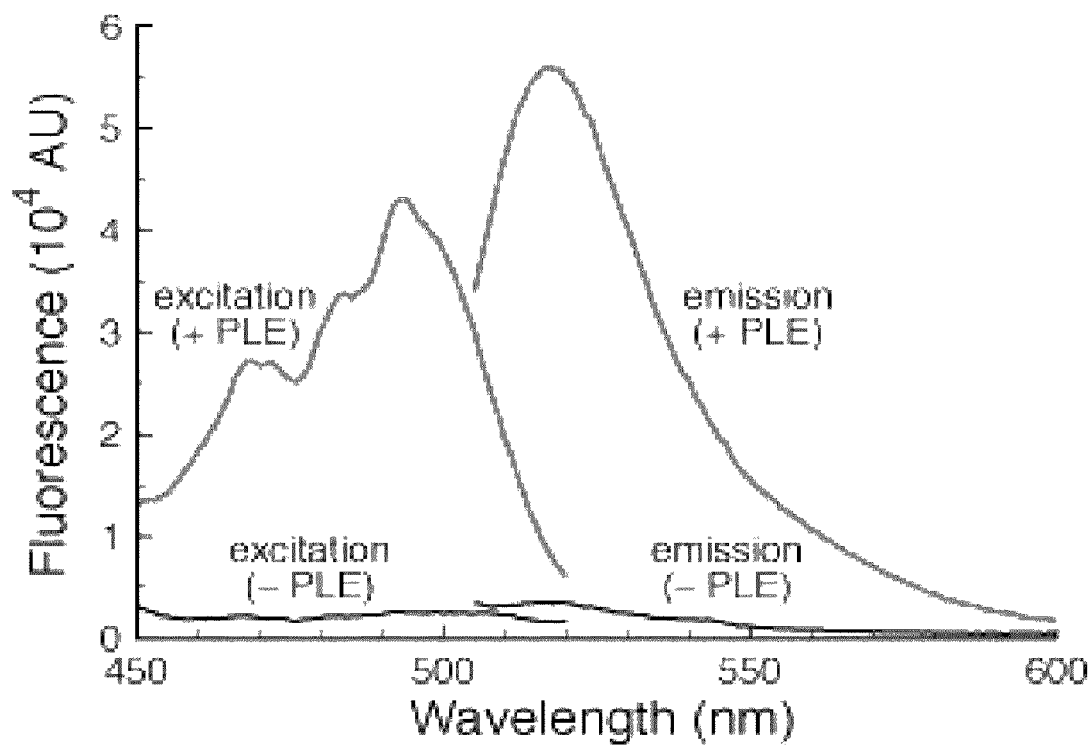
FIG. 1 shows excitation and emission spectra of (Ac-TML)$_2$—rhodamine before (+PLE) and after (−PLE) pig liver esterase (PLE)—catalyzed cleavage.

In the invention, a fluorescent compound is functionalized with one or more blocking groups and optionally one or more urea-containing groups. The one or more blocking groups attached to the fluorescent compound produce a latent fluorescent compound. The blocking group(s) are released by reaction with a trigger. In the most general form, shown below, F represents a fluorescent molecule which can have one or more groups attached thereto. These groups include one or more blocking groups (B) and optionally one or more urea-containing groups (U). The blocking groups may be the same or different. The urea-containing groups may be the same or different. There may also be other optional substituents on F that are not released by reaction with the trigger.

In the Scheme below, n is an integer from 1 to the maximum number of blocking groups that can be attached to F. m is an integer from 0 to the maximum number of urea-containing groups that can be attached to F. The maximum number of blocking groups, urea-containing groups and other substituents that can be attached to F depends on the chemical structure of F, as known in the art. The urea-containing groups may be further reacted with a desired molecule or group, including an electrophile, a protein, a peptide, or a nucleic acid, either before attaching the urea-containing group(s) to the fluorescent molecule or after the urea-containing group(s) are attached to the fluorescent molecule. The blocking group(s) are released from the latent fluorescent compound (II) by trigger T to form a fluorescent compound (I-U), which is detected by any suitable means such as fluorescence microscopy, fluorescence spectroscopy or other methods, as known in the art.

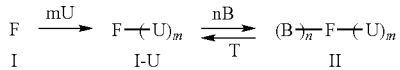

If a urea-containing group is not desired or required, fluorescent molecule F is reacted with one or more blocking groups B to form a latent fluorescent compound. In the Scheme below, F represents a fluorescent molecule which can have two identical blocking groups ($B_1$) attached thereto. $T_1$ represents the trigger.

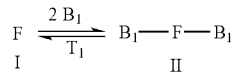

The reaction of compound II with the trigger $T_1$ releases the blocking groups and forms F which is detected.

The information provided herein allows for tailoring latent fluorescent compounds for analysis of different events using the same latent fluorescent molecule. Different blocking groups which are released with different triggers can be attached to the same fluorescent molecule, allowing determination of the presence of more than one different trigger. For example, see the Scheme below:

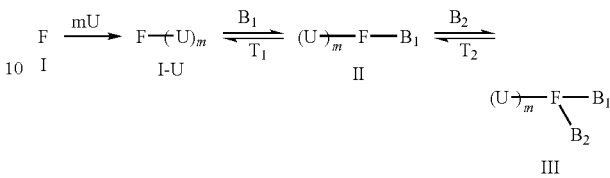

This Scheme shows the fluorescent molecule F reacting with one or more optional urea-containing groups U to form structure I-U. Structure I-U undergoes a reaction with blocking group $B_1$ to form structure II. Structure II has a fluorescence intensity lower than that of structure I and structure I-U. Blocking group $B_1$ is released with trigger $T_1$ to form fluorescent molecule I-U. If desired, the reaction can be stopped at this point to study $T_1$. Structure II also undergoes a further reaction with blocking group $B_2$ to form structure III. Structure III has a fluorescence intensity lower than that of structures I and I-U and a fluorescence different from structure II. Blocking group $B_2$ is released with trigger $T_2$. Structure III can be used to study both triggers $T_1$ and $T_2$, or only one trigger. Although in the Scheme above, two blocking groups and triggers are shown, it is to be understood that additional blocking groups and triggers can be used in an analogous manner.

It is understood that the reactions of the fluorescent molecule with one or more urea-containing groups and the reaction of the fluorescent molecule with one or more blocking groups can take place in any order. The order of reactions is conveniently determined by the chemical reactions that are used, and the order of reactions is easily determinable by one of ordinary skill in the art.

Fluorescent molecules which are useful in the invention include any molecule which has decreased fluorescence when one or more blocking groups are attached, and increased fluorescence when at least one blocking group is removed. Preferably, the molecule is non-fluorescent when one or more blocking groups are attached and fluorescent when all the blocking groups are removed. The one or more blocking groups are preferably attached to the fluorescent molecule though one or more covalent bonds, but other methods of attaching the one or more blocking groups to the fluorescent molecule are possible, as known in the art, such as ionic bonds. Fluorescent molecules useful in the invention contain, or can be modified to contain, functional or reactive groups to which the blocking group(s) may be attached or react with to form the latent fluorescent molecule and if optional urea-containing group(s) are attached, functional or reactive groups to which the urea-containing group(s) may be attached or react with. Suitable functional groups include, but are not limited to, amino groups, hydroxyl groups, carboxyl groups, phosphoryl groups, sulfuryl groups and azido groups. The blocking group can also contain a suitable functional group to attach or react it with the fluorescent molecule without a separate reactive group. The urea-containing group can also contain a suitable functional group to attach or react with the fluorescent molecule without a separate reactive group.

One class of fluorescent molecules useful in the invention is fluorescent molecules having the backbone structures shown in Scheme I. In the structures in Scheme I, the R's indicate various substituents, where at least one R is a functional group which allows attachment of a blocking group and if desired, at least one R is a functional group which allows attachment of a urea-containing group. The R's can be the same or different, and there may be one or more R on each ring. There does not need to be an R on each ring. Exemplary R substituents include hydrogen, optionally-substituted straight chain, branched and cyclic C1-20 alkyl, alkenyl, or alkynyl groups where one or more of the C atoms can be substituted, or wherein one or more of the C, CH or $CH_2$ moieties can be replaced with O atoms, —CO— groups, —OCO— groups, N atoms, amine groups, S atoms or a ring structure, which ring structure can optionally contain one or more heteroatoms and which ring structure can be optionally substituted; and optionally substituted aromatic and nonaromatic ring structures, including rings that are fused to one or more rings of the backbone structure shown in Scheme I, where the ring structure substitutions include those substituents defined as R above.

Two or more R groups can be linked to form one or more rings and such rings may contain one or more of the same or different heteroatoms, e.g., O atoms, S atoms, N atoms or NH groups.

R groups can in general be substituted with one or more of any chemical groups that do not negatively interfere with the function of the molecules herein. R groups can be, for example, substituted with one or more halogens, particularly fluorines; nitro groups; cyano groups; isocyano groups; thiocyano groups (—S—C≡N); isothiocyano groups (—N═C═S); azide groups; —$SO_2$ groups; —$OSO_3H$ groups; one or more optionally substituted straight-chain, branched or cyclic alkyl, alkenyl or alkynyl groups (particularly as substituents for aromatic or other cyclic ring structures); $OR^1$; —CO—$OR^1$; —O—CO—$R^1$; —$N(R^1)_2$; —CO—$N(R^1)_2$; —$NR^1$—CO—$OR^1$; —$SR^1$; —$SOR^1$; —$SO_2$—$R^1$; —$SO_3R^1$; —$SO_2N(R^1)_2$; —$P(R^1)_2$; —$OPO_3(R_1)_2$; and —$Si(R^1)_3$. Each $R^1$, independent of other $R^1$ in the substituent group can be a hydrogen, an optionally substituted straight-chain, branched or cyclic alkyl, alkenyl or alkynyl group wherein one or more C, CH or $CH_2$ groups therein can be replaced with an O atom, a —CO— group, a —OCO— group, a N atom, a S atom or an amine group; an optionally substituted aromatic group. Two or more $R^1$ groups can be linked together to form a ring which may contain one or more of the same or different heteroatoms. Optional substitution includes substitution with one or more halogens, nitro groups; cyano groups; isocyano groups; thiocyano groups (—S—C≡N); isothiocyano groups (—N═C═S); azide groups; —$SO_2$ groups; —$OSO_3H$ groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; various silyl groups, including alkyl-substituted silyl groups.

Some particular ring substituents include: —Br, —OH, —$SO_3$, isothiocyano, thiocyano, carboxylic acid and carboxylic acid derivatives, —$NH_2$, amines and —$NO_2$ and any salts thereof.

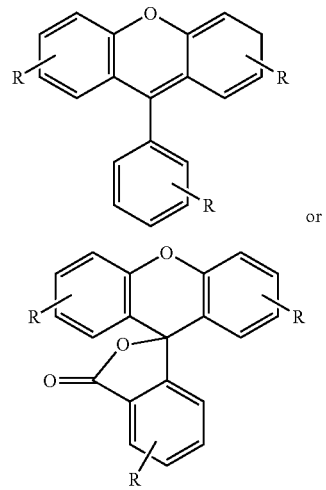

Scheme I

Substituents that are not involved in bonding or otherwise attaching to blocking groups or urea-containing groups may be attached to the fluorescent molecule and are useful for purposes such as adjusting the wavelength of fluorescence or absorbance or binding to a molecule or structure to be studied, for example a protein or nucleic acid. Such substituents are known in the art. Non-limiting examples of some biological applications of the invention are given in the Examples.

One class of fluorescent molecules useful in the present invention include molecules useful as fluorescent dyes. These molecules are known in the art and include fluorescein and fluorescein derivatives including fluorescein isothiocyanate derivatives, eosins and erythrosins, and carboxyfluorescein succinimidyl ester derivatives; xanthene and xanthene derivatives; rhodamine and rhodamine derivatives including texas red and texas red derivatives; acridines and acridine derivatives; flavins and flavin derivatives; alizarin and alizarin derivatives; coumarin and coumarin derivatives; quinacrine and quinacrine derivatives; and succinimidyl esters and carboxylic acids. Some of these molecules are shown below in Scheme II. It is noted that derivatives of fluorescent molecules can be made that allow bonding of the desired blocking group(s) and optional urea-containing group(s) in view of the disclosure herein and using methods of organic synthesis known in the art. These derivatives are apparent to one of ordinary skill in the art in view of the disclosure and these derivatives can be made using art known methods without undue experimentation.

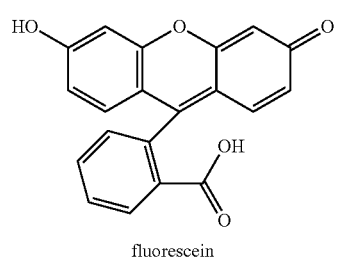

Scheme II fluorescein

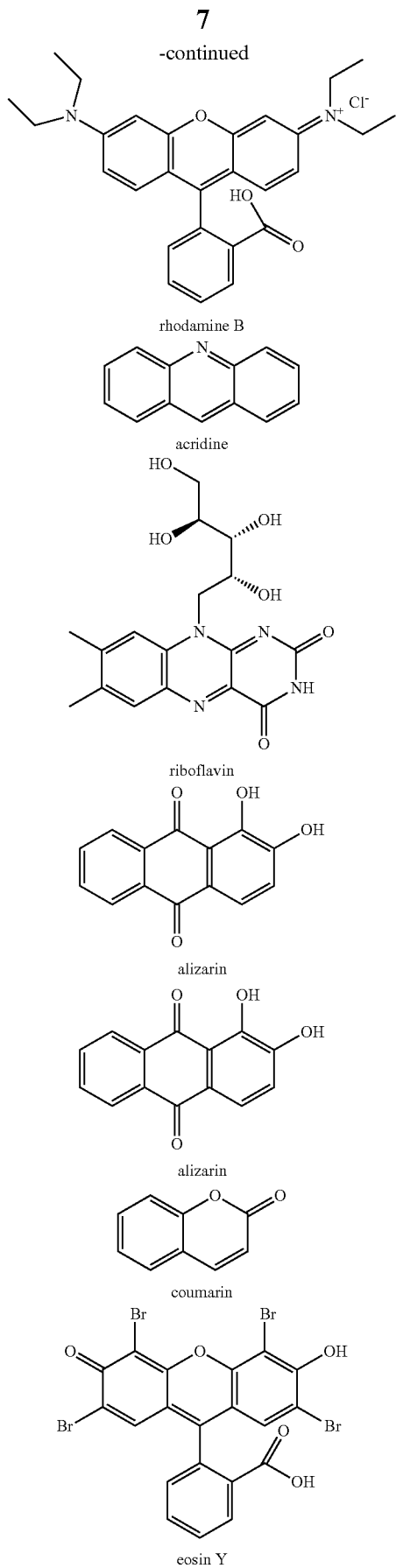
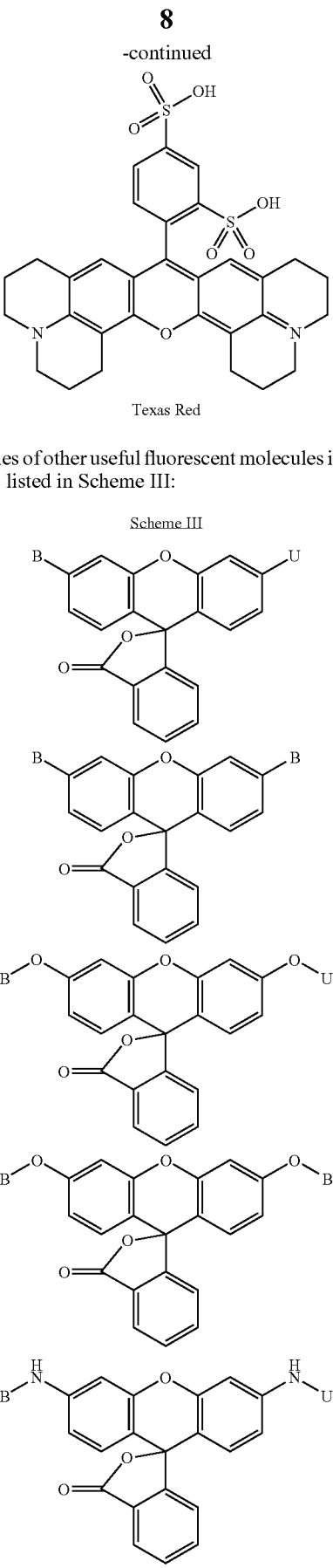
Examples of other useful fluorescent molecules include the molecules listed in Scheme III:
Scheme III

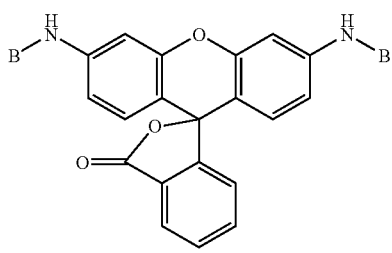

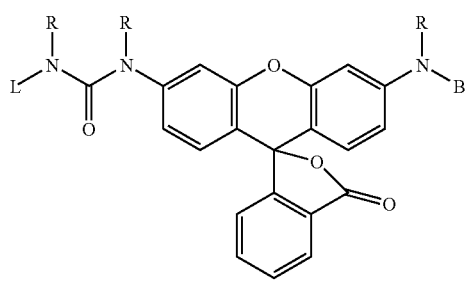

In the structures in Scheme III, B indicates a blocking group and U indicates a urea-containing group. It is understood that more than one blocking group may be attached to a fluorescent molecule and the blocking group(s) may be the same or different. It is understood that more than one urea-containing group may be attached to a fluorescent molecule and the urea-containing group(s) may be the same or different.

Other useful compounds are shown in Scheme IV. In Scheme VI, rhodamine and rhodol-based compounds are shown:

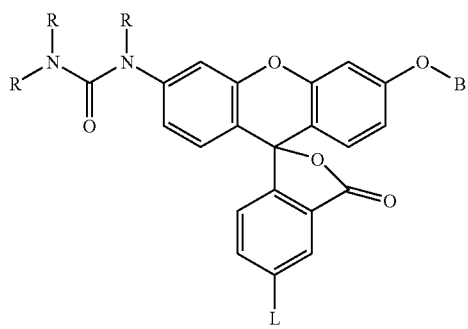

Scheme IV

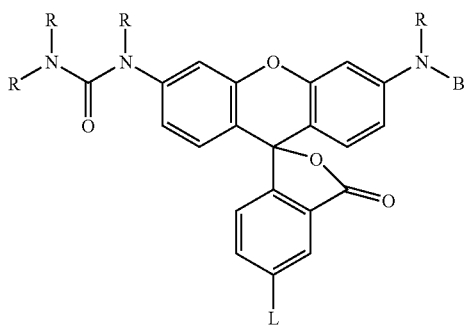

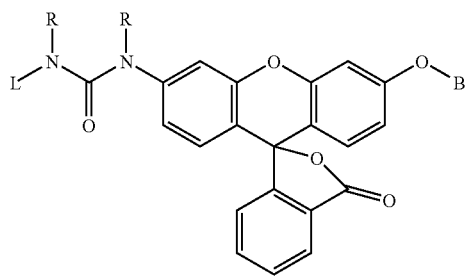

In Scheme IV, L is a linking group such as that defined for R above, and B is a blocking group. R is as defined above.

A specific example of useful latent fluorescent compounds having a rhodamine backbone includes the following structure:

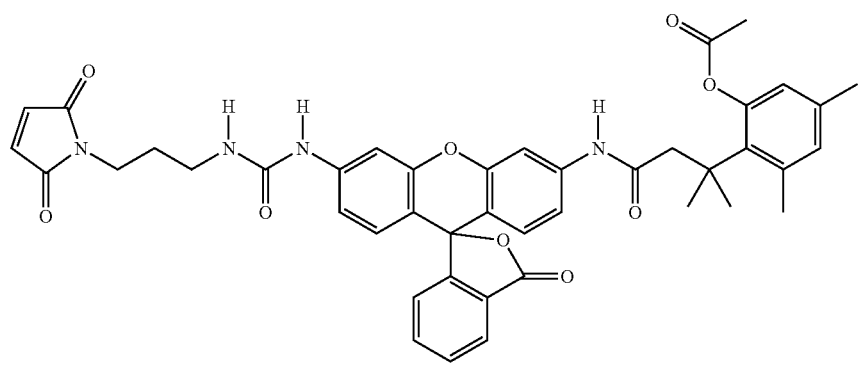

One or more blocking groups and one or more optional urea-containing groups can be attached to dye backbone structures, including those dye backbone structures shown below in Scheme V, using procedures known in the art:

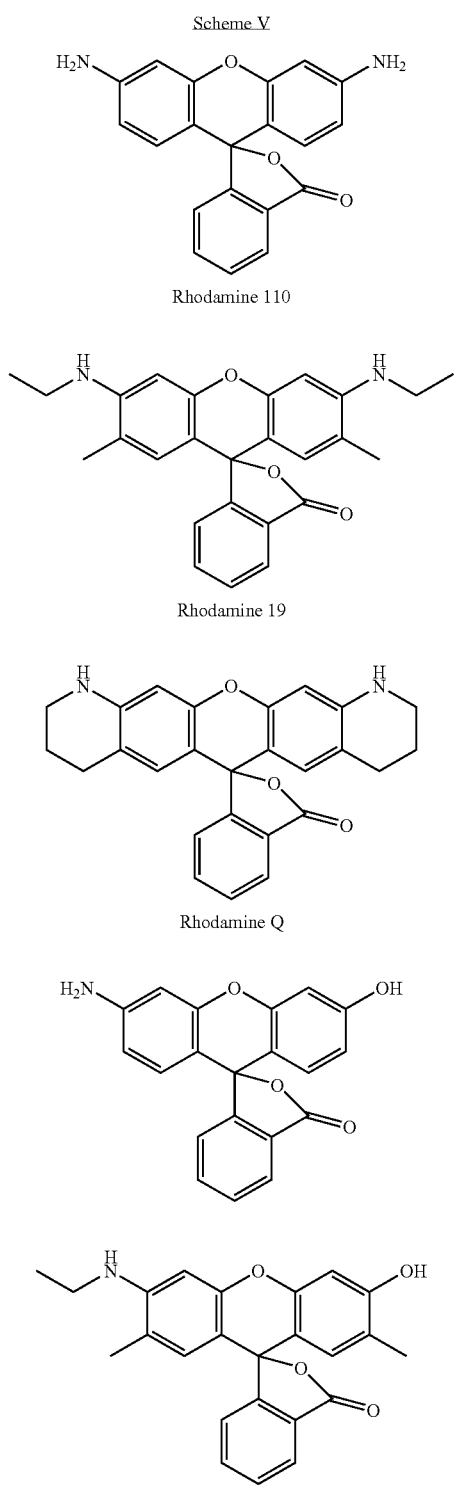

The rhodamine and rhodol backbone structures, as well as other fluorescent molecule structures can be extended by adding additional rings, as shown below in Scheme VI:

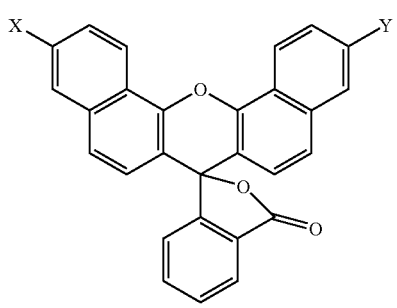

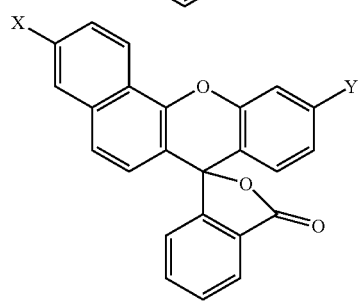

In particular compounds given by the structures in Scheme VI, X and Y are both N or one of X and Y is N and the other of X and Y is O. Other useful substituents are known in the art.

Coumarin backbone structures are also useful in the present invention. A general structure of a compound having the coumarin backbone structure is shown below:

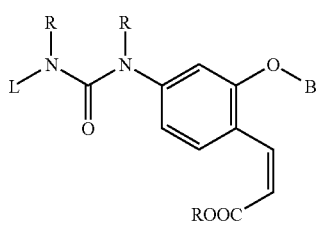

where R, B and L are as defined above.

Removal of the blocking Group B in the coumarin backbone causes cyclization to form the coumarin structure. Some examples of the backbone coumarin structures are shown below in Scheme VII:

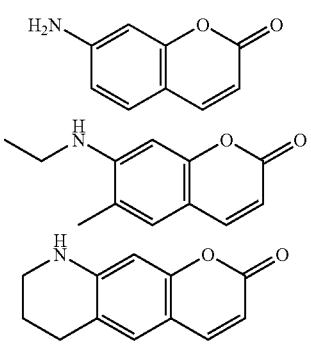

Oxazine-based compounds are also useful in the present invention. General structures and the backbone dye structures resulting from removal of blocking group B are shown in Scheme VIII:

Scheme VIII

General Structures:

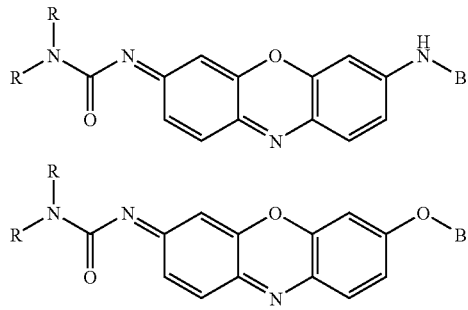

Parent Dye Structures:

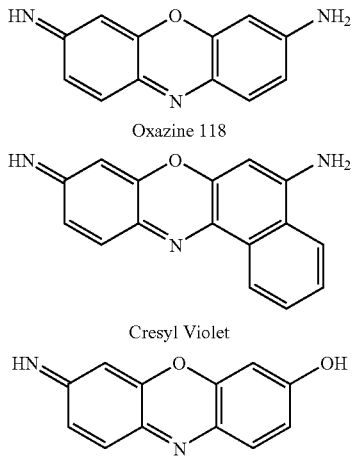

Oxazine 118

Cresyl Violet

Other useful latent fluorescent compounds and backbones include the structures listed in Scheme IX:

Scheme IX

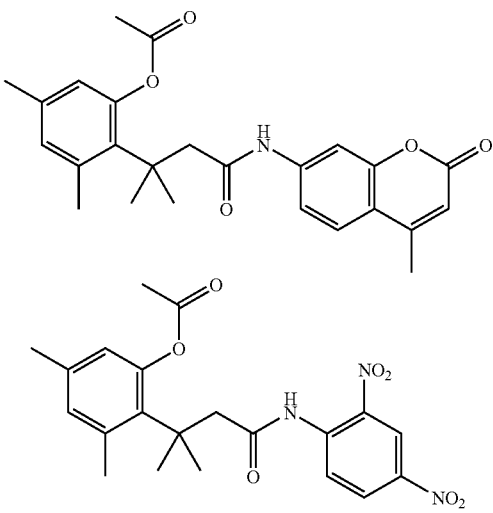

-continued

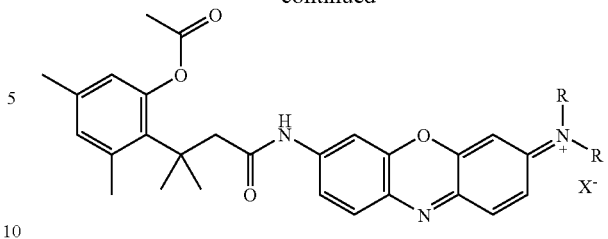

In Scheme IX, R can be generally any optionally substituted R group as above and X⁻ is a counter anion, for example, X is a halogen.

All latent fluorescent compounds described herein can be used in the methods described herein.

Blocking groups and triggers are selected so that the blocking group and trigger react together to release the blocking group from the latent fluorescent molecule. Blocking groups useful in the invention are those groups that contain a particular reactive group that reacts with the trigger to break the bond(s) attaching the blocking group to the latent fluorescent molecule. Some particular blocking group/trigger combinations include trialkyl lock-containing compounds that are used with a esterase trigger; —$PO_3^{2-}$ containing blocking groups that are used with a phosphatase trigger such as alkaline or acid phosphatase; —$PPh_2$ containing blocking groups that are used with an azide trigger; β-D-galactose containing blocking groups that are used with a β-D-galactosidase trigger; α-D-mannose containing blocking groups that are used with an α-D-mannosidase trigger; β-D-glucose containing blocking groups that are used with a β-D-glucosidase trigger; glycosyl-containing blocking groups that are used with a thioglucosidase trigger; carbobenzoxy (CBZ)-glycine-arginine containing blocking groups that are used with a thioglucosidase trigger; leucine containing blocking groups that are used with a leucineaminopeptidase trigger; adenosine-5'-phosphate containing blocking groups that are used with a snake venom phosphodiesterase trigger; alkyl groups that are used with a cytochrome P450 enzyme trigger; and nucleoside-3'-phosphate containing blocking groups that are used with a nuclease or ribonuclease trigger. Other blocking groups include: phosphoryl, sulfuryl, glycosyl, peptidyl, nucleotidyl, which are used with a wide variety of triggers, as known in the art.

One class of blocking groups contains a steric lock. A steric lock is used to position groups sterically to bias reactivity so that a desired reaction is more likely to occur than if the steric lock was not present. Steric locks include groups having multiple substitution such as alkyl or aryl groups, forming trialkyl or triaryl locks, as described below. Steric locks include those substituted carboxylic acids having a tertiary substituted beta carbon and a secondary substituted delta carbon according to the general formula below:

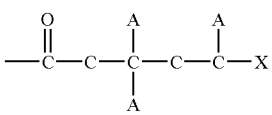

wherein A is as defined below and each A may be the same or different and the valencies of the carbon atoms are satisfied through hydrogen atoms or other substituents, including formation of a ring structure with another part of the molecule. X is a hydrogen atom, a carbon-containing unit or a carbon-heteroatom unit, including a ring structure formed with another part of the molecule. Steric locks having an alcohol, amine or thiol substitution in a sterically available position undergo a lactonization reaction upon a suitable trigger such as an esterase. The lactonization reaction of a steric lock is known in the art.

In the structure above, A is independently a C1-12 straight chain or branched optionally substituted alkyl or optionally substituted alkoxy, C3-8 optionally substituted cycloalkyl, halogen, optionally substituted aryl, or optionally substituted aralkyl (containing both an aryl group and an alkyl group). All A groups can be the same or different. One class of steric lock contains three alkyl A groups (forming a trialkyl lock). One class of trialkyl lock contains small alkyl groups, defined as C1-C5 alkyl or alkoxy groups. In one embodiment, all A groups are methyl groups. One class of steric lock contains one or more aryl groups, including phenyl rings. One class of steric lock contains one or more halogen atoms and halogen atom-containing groups. Optional substituents on the A groups are one or more of halogen, nitro, cyano, carboxy, carboxylalkyl, alkylcarbonyl, heteroatom and other substituents that do not prevent the steric lock from performing the desired function. Heteroatoms are preferably O, N, S, or P. The optional substituents may be the same or different. The operation of the steric lock is described below. The substituents on the steric lock are those that do not prevent the steric lock from performing its desired function, as described below.

One particular example of a steric lock is a "trimethyl lock" having an o-hydroxycinnamic acid derivative (1) where unfavorable steric interactions between the three methyl groups encourage rapid lactonization to form a hydrocoumarin (2) (see Scheme X below). This intramolecular reaction has an effective molarity near $10^{15}$ M.

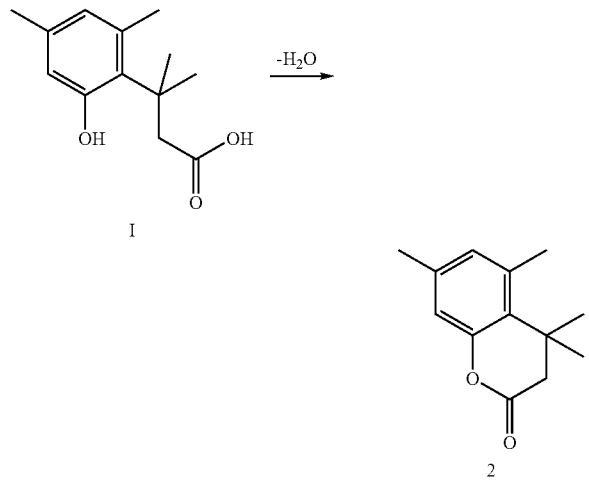

Scheme X

In one embodiment of this invention, the fluorescent molecule contains a urea group. In a more specific embodiment the urea group has the structure:

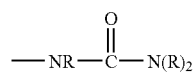

or anions and salts thereof, where each R, independent of any other R, are selected from the exemplary group consisting of:

hydrogen, straight-chain, branched or cyclic C1-C20 alkyl groups in which one or more of the carbon atoms are optionally substituted with non-hydrogen substituents and wherein one or more C, CH or $CH_2$ moieties can be replaced with an O atom, a —CO— group, a —OCO— group, a nitrogen atom, an $NR^1$ group, or a S atom;

straight-chain, branched or cyclic C1-C20 alkenyl group which contains one or more double bonds in which one or more of the carbon atoms are optionally substituted with non-hydrogen substituents and wherein one or more C, CH or $CH_2$ moieties can be replaced with an O atom, a —CO— group, a —OCO— group, a nitrogen atom, an $NR^1$ group, or a S atom;

straight-chain, branched or cyclic C1-C20 alkynyl group which contains one or more triple bonds in which one or more of the carbon atoms are optionally substituted with non-hydrogen substituents and wherein one or more CH or $CH_2$ moieties can be replaced with an O atom, a —CO— group, a —OCO— group, a nitrogen atom, an $NR^1$ group, or a S atom; and an optionally substituted aromatic or heteroaromatic ring structure or non-aromatic ring structure, including rings that are fused, particularly rings that are fused to one or more rings of a backbone structure shown in structures above, for example, Scheme 1.

Two or more R groups can be linked to form one or more rings and such rings may contain one or more of the same or different heteroatoms, e.g., O atoms, S atoms, N atoms or NH groups.

R groups can in general be substituted with one or more of any chemical groups that do not negatively interfere with the function of the molecules herein. R groups can be, for example, substituted with one or more halogens, particularly fluorines; nitro groups; cyano groups; isocyano groups; thiocyano groups (—S—C≡N); isothiocyano groups (—N=C=S); azide groups; —$SO_2$ groups; —$OSO_3H$ groups; one or more optionally substituted straight-chain, branched or cyclic alkyl, alkenyl or alkynyl groups (particularly as substituents for aromatic or other cyclic ring structures); $OR^1$; —CO—$OR^1$; —O—CO—$R^1$; —N$(R^1)_2$; —CO—N$(R^1)_2$; —$NR^1$—CO—$OR^1$; —$SR^1$; —$SOR^1$; —$SO_2$—$R^1$; —$SO_3R^1$; —$SO_2N(R^1)_2$; —P$(R^1)_2$; —$OPO_3(R_1)_2$; and —Si$(R^1)_3$. Each $R^1$, independent of other $R^1$ in the substituent group can be a hydrogen, an optionally substituted straight-chain, branched or cyclic alkyl, alkenyl or alkynyl group wherein one or more C, CH or $CH_2$ groups therein can be replaced with an O atom, a —CO— group, a —OCO— group, a N atom, a S atom or an amine group; an optionally substituted aromatic group. Two or more $R^1$ groups can be linked together to form a ring which may contain one or more of the same or different heteroatoms. Optional substitution includes substitution with one or more halogens, nitro groups; cyano groups; isocyano groups; thiocyano groups (—S—C≡N); isothiocyano groups (—N=C=S); azide groups; —$SO_2$ groups; —$OSO_3H$ groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; various silyl groups, including alkyl-substituted silyl groups.

In specific embodiments, R groups are hydrogens or optionally substituted C1-20 alkyl or alkenyl groups, including cyclic alkyl and alkenyl groups in which one or more C, CH or $CH_2$ groups are replaced with one or more O atoms, —CO— groups, —O—CO-groups, N atoms, or S atoms. In specific embodiments R groups contain one or more 5- and 6-member alkyl or alkenyl rings in which in which one or more C, CH or $CH_2$ groups are replaced with one or more O atoms, —CO— groups, —O—CO-groups, N atoms, or S atoms. In specific embodiments, R groups can carry one or more substituents that are electrophiles. A variety of electrophilic groups are known in the art.

Some particular urea structures that are useful in the invention include:

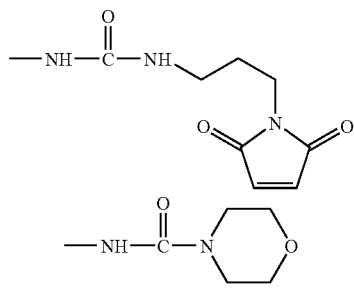

and the urea structures disclosed in U.S. Pat. No. 4,714,763, which is incorporated by reference to the extent not inconsistent with the disclosure herewith. Urea structures include the urea group structure:

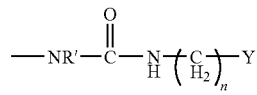

where R' is hydrogen or an alkyl group with from 1 to 10 carbons; n is an integer from 0 to 20; Y is —N=C=O, —N=C=S, carboxylic acid, or salt thereof, primary or secondary amine, or salt thereof, or an optionally substituted ring structure that may contain heteroatoms in the ring.

The urea group can be used to attach further groups to the molecule to provide desired functionality. For example, a protein, peptide or nucleic acid can be attached to the urea group using methods known in the art to one skilled in the art of organic synthesis. An electrophile can be attached to the urea group using methods known in the art to one skilled in the art of organic synthesis. The urea-containing group allows a molecule of interest (such as a protein, peptide, or nucleic acid) to be attached to the fluorescent molecule. The molecule of interest can then be studied, using a combination of the blocking group and trigger, as described herein. An example of the preparation of urea-containing groups and urea-containing groups coupled to biological molecules is described in U.S. Pat. No. 4,714,763 and references cited therein, all of which are specifically incorporated by reference to the extent not inconsistent with the disclosure herewith.

One embodiment of the invention is a latent fluorescent molecule having one or more optional urea-containing group(s) chemically bonded to the fluorescent core and at least one blocking group chemically bonded through a cleavable linker on the fluorescent core. In one embodiment, the urea-containing group is chemically bonded to a molecule of interest. Upon activation by an appropriate trigger, the cleavable linker is cleaved and releases the blocking group. This results in formation of an active fluorescent molecule. Detection of the fluorescence from the active fluorescent molecule is an indirect detection of the trigger.

Another embodiment of the invention is a latent fluorescent molecule having one or more optional urea-containing group(s) and at least one blocking group chemically bonded through an amide bond on the fluorescent core. In one embodiment of the invention the blocking group having an amide bond contains a steric lock. Upon activation by an appropriate trigger, the amide bond is cleaved. This results in formation of an active fluorescent molecule.

The methods and compounds of the invention can be used to study protein systems, where the latent fluorescent compound is attached to a protein, and the fluorescence of the system can be used to track protein movement. In a currently available assay, a protein is tagged with rhodamine or fluorescein, and there is a large background fluorescence signal which interferes with the desired fluorescence measurements. Using the invention described herein, there would be no background fluorescence signal from the protein to which a latent fluorescent compound is attached, or the background fluorescence signal would be small, and the fluorescent molecule is released when the substrate is exposed to the particular trigger which releases the blocking groups from the latent fluorescent molecule. For example, in a fluorescent probe system using an esterase as the trigger, since esterases are present in the cytosol, but not outside the cell, no fluorescence would be detected until the latent fluorescent compound crossed the cell membrane and was exposed to the trigger. The esterase-triggered system can be attached to a virus using the urea-containing group or other group on the fluorescent molecule, using methods known in the art and fluorescence microscopy can be used to study where and when the contents of the virus contact the contents of the cytosol of a human cell (which contains the esterase) during an infection. In addition, the urea-containing group can be used to covalently attach proteins or peptides to follow the proteins or peptides as they travel through cells. Suitable urea-containing groups which bond to the latent fluorescent molecule and attach to proteins or peptides, and methods of preparation thereof are known to the art.

Although the invention is described in detail herein using latent fluorescent molecules, another embodiment of the invention is the use of molecules which have a different absorbance spectra when one or more blocking groups are attached. In this embodiment, the difference in absorbance spectra can be used to determine if the blocking groups have been removed by reaction with the trigger. A difference in the visible absorbance of a molecule when one or more blocking groups are attached is particularly convenient for rapid testing for the presence of a particular trigger. In this embodiment, no external measuring devices would be necessary, the human eye could act as the detector, or a spectrophotometer could be used, as known in the art. An example of this embodiment is described in the Examples section below. Any molecule which has a different detectability when blocking groups are attached may be used in the invention. One or more urea-containing groups can be used to attach a group of interest to the absorbing molecules.

EXAMPLES

Esterase Assay Using Trimethyl Lock

In this example, rhodamine was linked to two trimethyl lock-containing compounds through amide bonds, using the procedure described below. The amide bonds linking the trimethyl lock-containing compounds to the rhodamine backbone cleave rapidly upon reaction with an esterase trigger, releasing rhodamine. In the trimethyl lock system, steric strain from the three methyl groups forms a lactone, which releases the amines of the rhodamine through acyl transfer. These reactions are shown generally in Scheme XI, where the R groups are as defined above.

The rhodamine amide has negligible fluorescence, but upon release of the blocking groups, the fluorescence increased by approximately 1000 times.

In a particular example, Rhodamine 110 was used as the fluorescent compound. The amide groups of N,N-diacetylated rhodamine 110, which has been used as a protease substrate, are stable in a HeLa cell extract (data not shown). Nonetheless, the trimethyl lock is capable of effecting rapid N→O acyl transfer to liberate an amine upon formation of lactone 2. Hence, the trimethyl lock can link the unmasking of the phenolic oxygen with the production of rhodamine 110 by N→O acyl transfer. Esterases were chosen as the activating

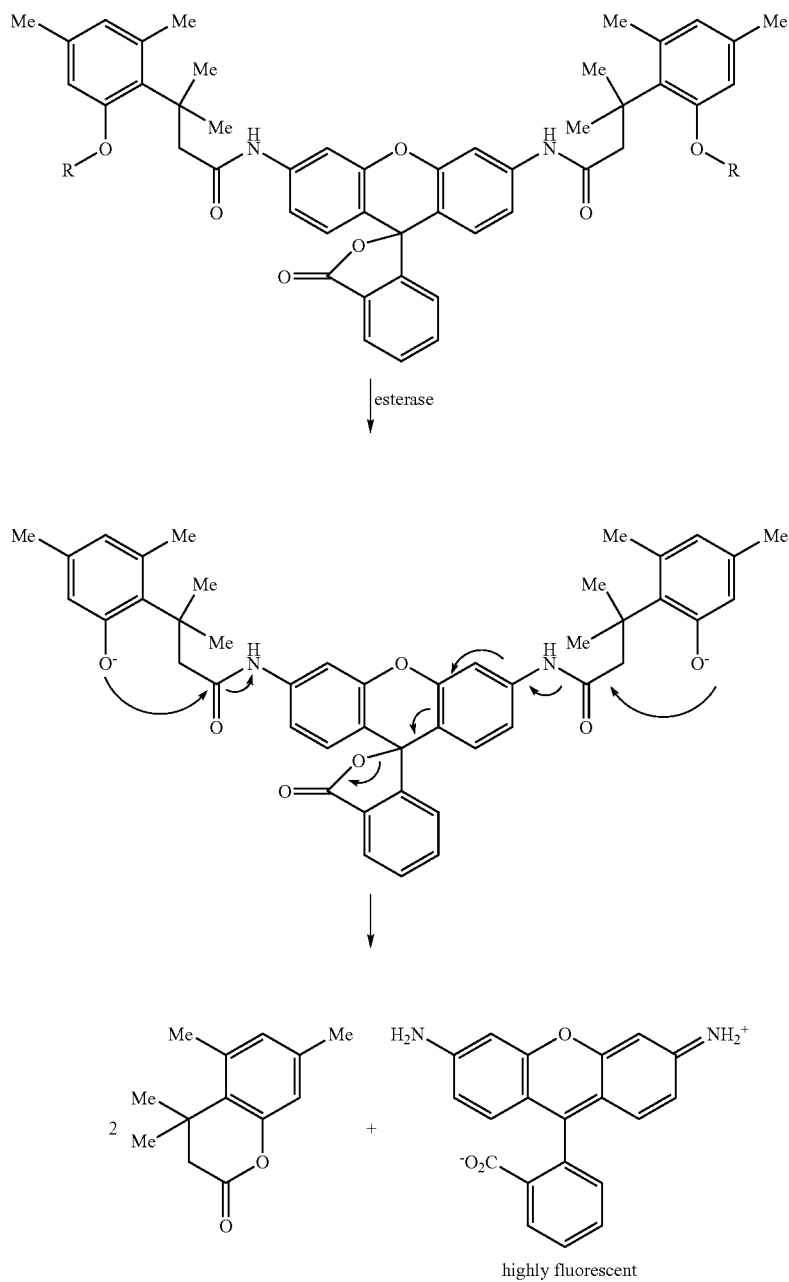

enzyme, due to their high abundance in the mammalian cytosol and known utility in pro-drug strategies. Accordingly, profluorophore 3 was synthesized as a putative esterase substrate by condensation of rhodamine 110 with excess O-acetylated 1 (Scheme XII). Compounds 1 and 2 are shown in Scheme X.
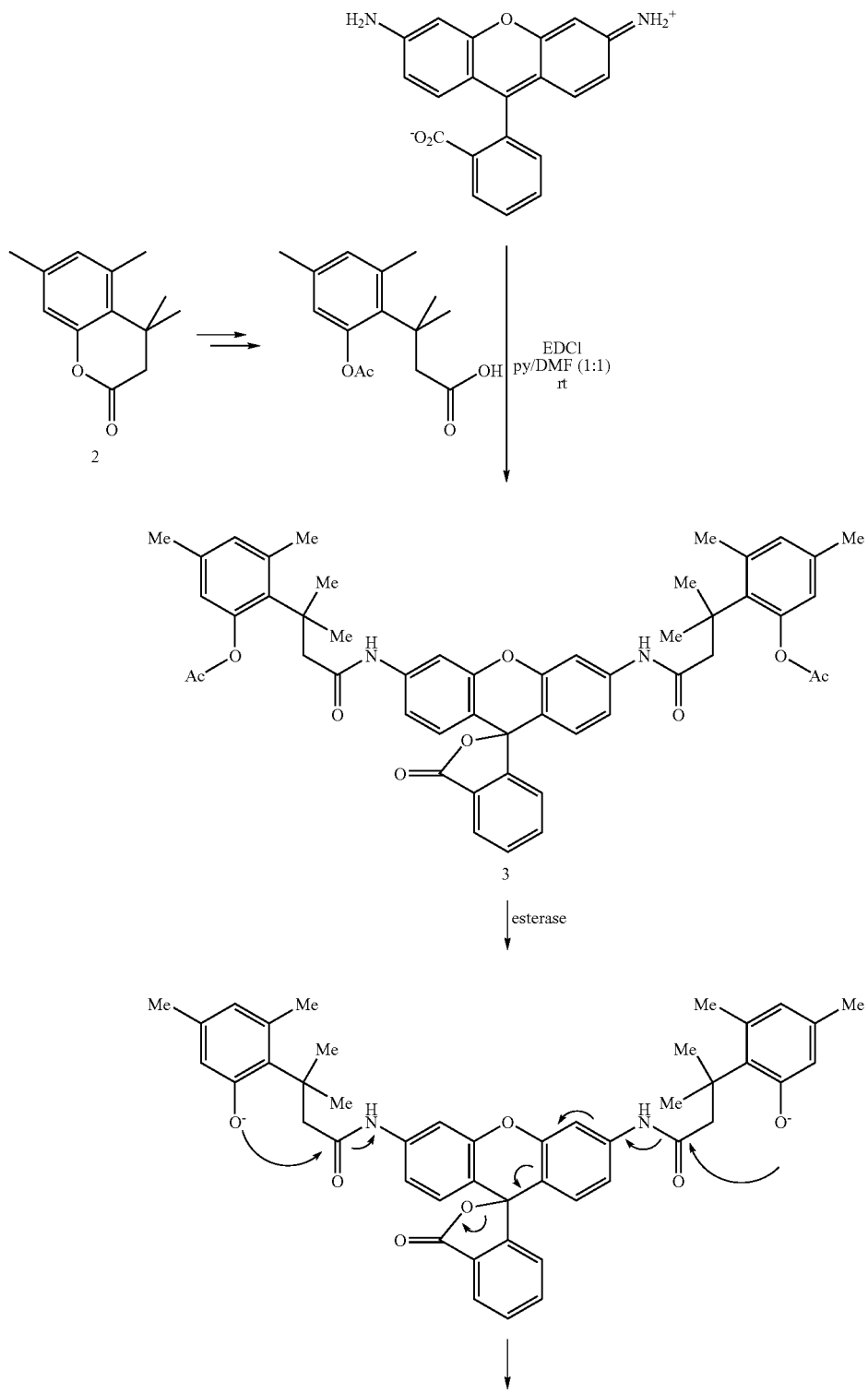

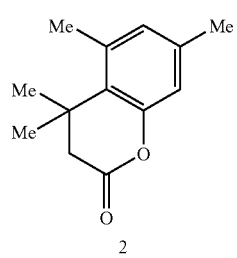

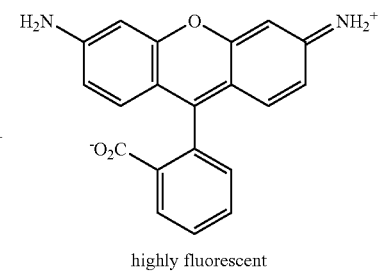

2                            highly fluorescent

The fluorescence spectrum of pro-fluorophore 3 exhibited near-baseline excitation and emission (FIG. 1), even after months of storage in phosphate-buffered saline (PBS). Introduction of pig liver esterase (PLE) to the solution resulted in a large increase in fluorescence with apparent kinetic parameters of $k_{cat}/K_M = 1.9 \times 10^3$ $M^{-1}s^{-1}$ and $K_M = 0.47$ μM. Thus, pro-fluorophore 3 is a useful latent fluorophore—a stable molecule with intense fluorescence that is unmasked by a user-designated chemical reaction.

Figure 3A:
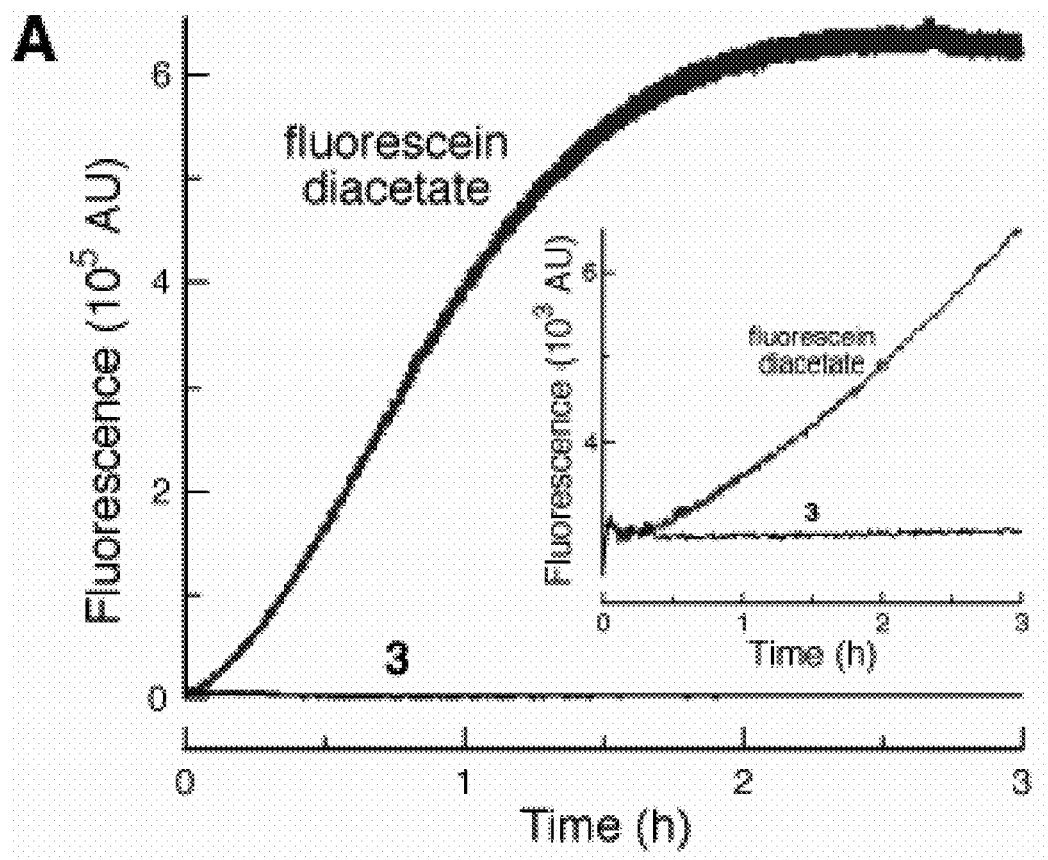
FIG. 3A shows the time-course of the generation of fluorescence ($\lambda_{ex}$ 492 nm, $\lambda_{em}$ 520 nm) by fluorescein diacetate (top curves in both graphs; 5 µM) and pro-fluorophore 3 (bottom curves in both graphs; 5 µM) in DMEM or PBS (inset).

The biological utility of pro-fluorophore 3 was then studied. To be useful, a latent fluorophore must remain non-fluorescent or have a small fluorescence in a biological environment. Accordingly, the accumulation of fluorescence in Dulbecco's modified Eagle's medium (DMEM) and phosphate-buffered saline (PBS) containing either fluorescein diacetate (which is a widely used pro-fluorophore) or 3 were studied. Solutions containing fluorescein diacetate became fluorescent in minutes (FIG. 3A). In contrast, solutions containing 3 lacked fluorescence after 3 h, indicative of a high stability for 3 in a biological environment.

Figure 3B:
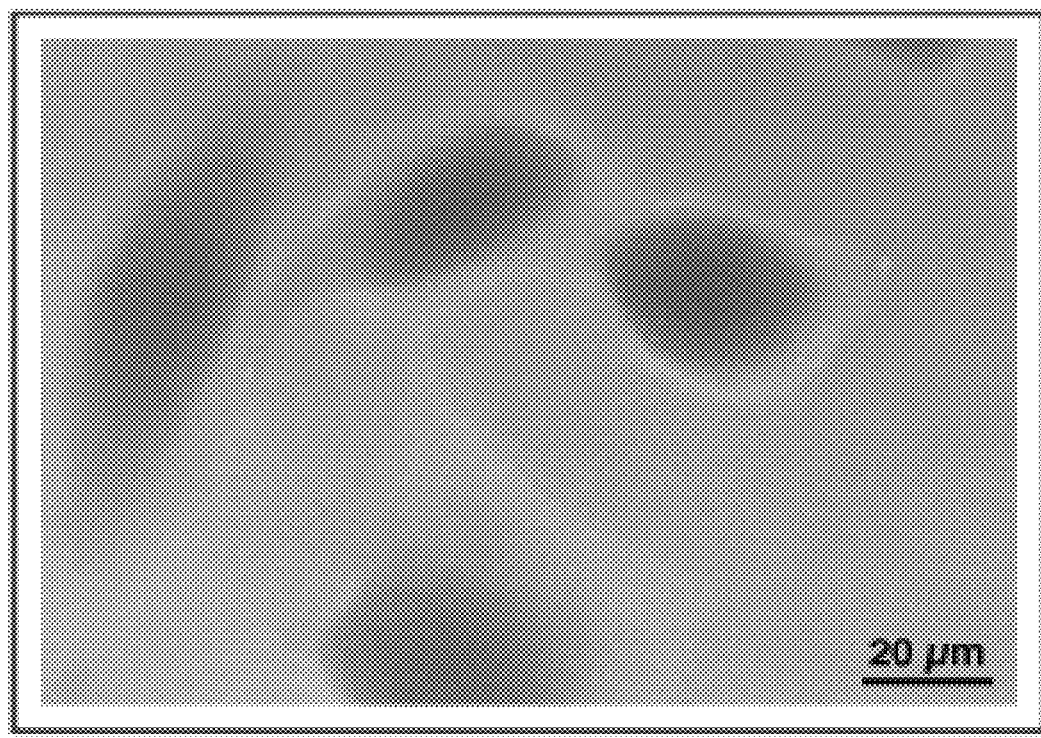
FIGS. 3B and C show unwashed HeLa cells incubated for 2 h with fluorescein diacetate (panel B; 10 µM) or 3 (panel C; 10 µM) at 37° C. in DMEM (5% $CO_2$, 100% humidity).
Figure 3C:
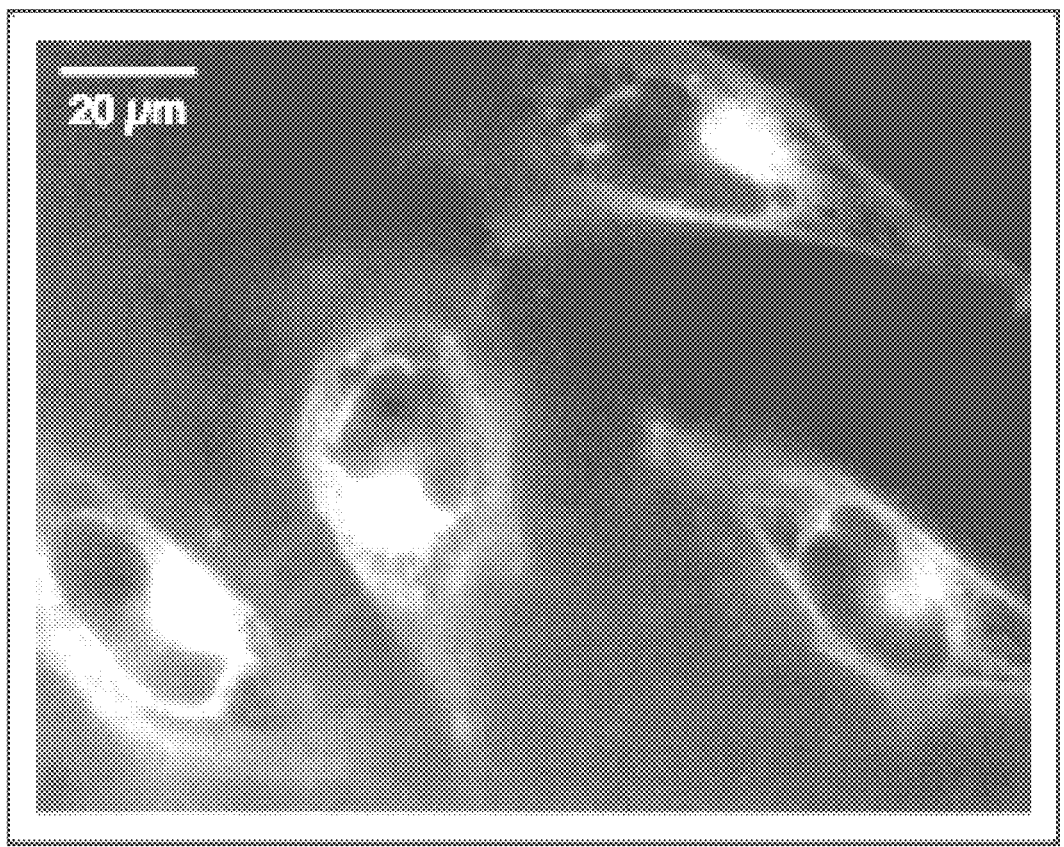
In FIG. 3C, the grey/white areas show the intensity of the fluorescence with the highest fluorescence shown as the lightest shade.
Figure 3D:
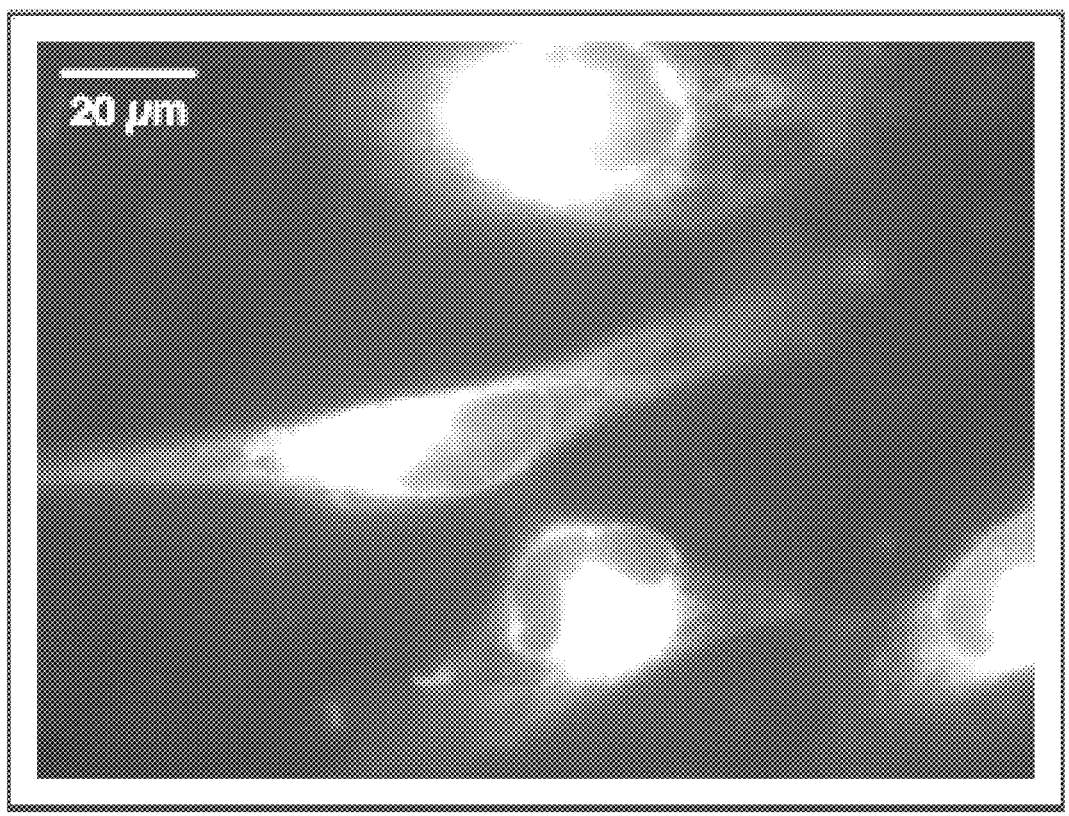
FIG. 3D shows washed HeLa cells incubated for 2 h with 3 (10 µM), and counter-stained with LysoTracker Red and Hoescht 33342.

Fluorescence microscopy was used to determine the fate of fluorescein diacetate and pro-fluorophore 3 in DMEM containing HeLa cells. The manifestation of fluorescence from fluorescein diacetate was much greater in the medium than in HeLa cells (FIG. 3B). In contrast, HeLa cells incubated with 3 displayed marked fluorescence, while extracellular regions remained non-fluorescent (FIG. 3C). Intracellular fluorescence was absent in the nucleus but strong in the cytosol and lysosomes (FIG. 3D), indicative of high esterase activity in these subcellular compartments.

Synthesis of Pro-Fluorophore 3

Pro-Fluorophore 3 was synthesized by the route shown in Scheme X and Scheme XII. Specifically, acetylated 1 (5 g, 18.8 mmol) was dissolved in a 100 mL of a 1:1 mixture of dry pyridine/DMF at room temperature under argon and treated with 1-ethyl-3-(3-dimethylaminopropyl) carbodiimide (EDCI, 3.6 g, 18.8 mmol). After stirring the resulting solution at room temperature for 1 h, rhodamine 110 (1.72 g, 4.7 mmol) was added. The reaction mixture was stirred at room temperature for 2 days under Ar(g), during which time the deep red solution slowly turned to a light peach color. The reaction mixture was treated with 100 mL of ethyl acetate and kept at −20° C. for 12 h. The clear liquid was decanted out and washed with 100 mL of 0.1 M HCl, followed by 100 mL of water. The organic layer was dried over $MgSO_4(s)$ and concentrated to dryness by rotary evaporation under reduced pressure. The red residue was purified by flash chromatography to yield pro-fluorophore 3 as a white solid (1.12 g, 29% yield). $^1H$ NMR ($CDCl_3$) δ 1.69 (s, 12H), 2.24 (s, 6H), 2.38 (s, 6H), 2.41 (s, 6H), 2.55 (s, 4H), 6.53-6.63 (m, 6H), 6.80 (s, 2H), 7.06 (d, J=6.9 Hz, 1H), 7.34 (s, 2H), 7.42 (s, 2H), 7.59 (m, 2H), 7.97 (d, J=6.9 Hz, 2H); $^{13}C$ NMR ($CDCl_3$) δ 172.2, 169.8, 153.1, 151.6, 150.1, 140.1, 139.1, 137.3, 134.9, 133.2, 132.8, 129.6, 128.1, 124.9, 123.9, 123.4, 115.1, 113.7, 107.2, 51.1, 40.4, 32.2, 32.1, 25.5, 21.9, 20.2.

Excitation-Emission Spectra of Pro-Fluorophore 3 in the Absence and Presence of Pig Liver Esterase A solution of pro-fluorophore 3 (5 μM) in 2 mL PBS was treated with PLE (0.5 μg), and the mixture was kept at room temperature for 4 h. The fluorescence excitation-emission spectra of the solution were recorded. The procedure was repeated for a solution of pro-fluorophore 3 treated in an identical manner, except for the addition of PLE.

Kinetic Parameters for Activation of Pro-Fluorophore 3 by Pig Liver Esterase

Figure 2:
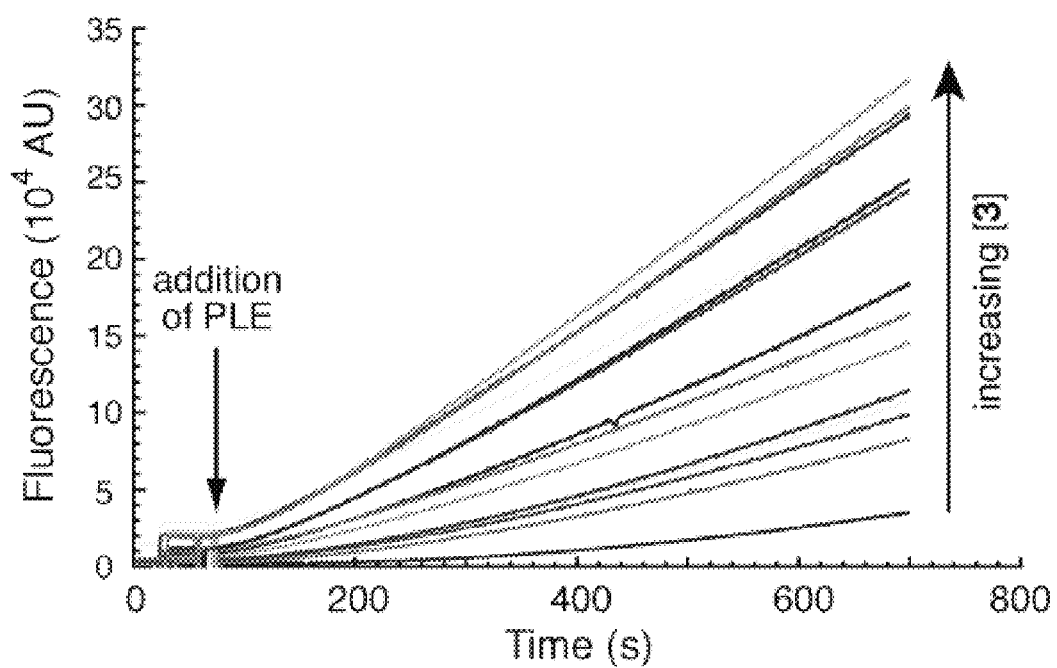
FIG. 2 shows raw data showing the change in fluorescence ($\lambda_{ex}$ 492 nm, $\lambda_{em}$ 520 nm) upon addition of PLE (0.5 mg/mL) to solutions containing various concentrations of pro-fluorophore 3.

All kinetic measurements were performed at room temperature at an excitation wavelength of $\lambda_{ex} = 492$ nm and an emission wavelength of $\lambda_{em} = 520$ nm in 2.0 mL of PBS containing PLE (2.5 μg/mL). A calibration curve was created by measuring the fluorescence of known concentrations of rhodamine-110 in the aforementioned reaction mixture. The rate of cleavage of 3 by PLE was measured adding known concentrations of 3 (50 nM-5 mM) to the reaction mixture and recording the rate of change of fluorescence. The corresponding rate of concentration change was calculated by applying the standard calibration curve for rhodamine-110. The enzymatic parameters were calculated by fitting the linear portion of the data (which corresponds to the Michelis-Menten equation). The data are shown in FIG. 2. Concentrations used and the steady state slope are shown in Table 1.

TABLE 1

| Concentration of (Ac-TML)$_2$-rhodamine (μM) | Steady State Slope (μM/s) |
|---|---|
| 0.05 | $3.81 \times 10^{-6}$ |
| 0.15 | $3.90 \times 10^{-6}$ |
| 0.25 | $4.42 \times 10^{-6}$ |
| 0.40 | $7.19 \times 10^{-6}$ |
| 0.50 | $7.37 \times 10^{-6}$ |
| 1.0 | $7.95 \times 10^{-6}$ |
| 1.5 | $9.89 \times 10^{-6}$ |
| 2.0 | $11.48 \times 10^{-6}$ |
| 2.5 | $11.09 \times 10^{-6}$ |
| 3.5 | $11.96 \times 10^{-6}$ |
| 4.5 | $12.75 \times 10^{-6}$ |
| 5.0 | $13.96 \times 10^{-6}$ |

The preparation and use of other useful compounds is described next. Preparation of Compound A:

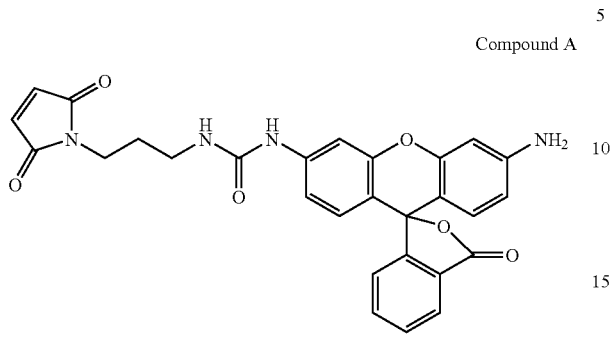

Compound A

4-Maleimidobutyric acid (1.49 g, 8.17 mmol) was dissolved in anhydrous THF (20 mL). To the THF solution was added N,N-diisopropylethylamine (1.90 mL) and Diphenyl phosphoryl azide (2.25 g, 8.17 mmol). The resulting solution was stirred at ambient temperature for 5 hours. Rhodamine 110 (1.0 g, 2.73 mmol) was then added in 10 mL of anhydrous DMF and the reaction flask was fitted with a reflux condenser and heated to 80° C. for 4 hours. Removal of the solvents under reduced pressure gave an orange solid that was purified via silica gel column chromatography using EtOAc and 10:1 CHCl$_3$:MeOH as eluents. The purification afforded 206 mg of the desired product as an orange crystalline solid (yield: 15%). MS, m/z=511.2 (M+H$^+$).

Preparation of Compound B:

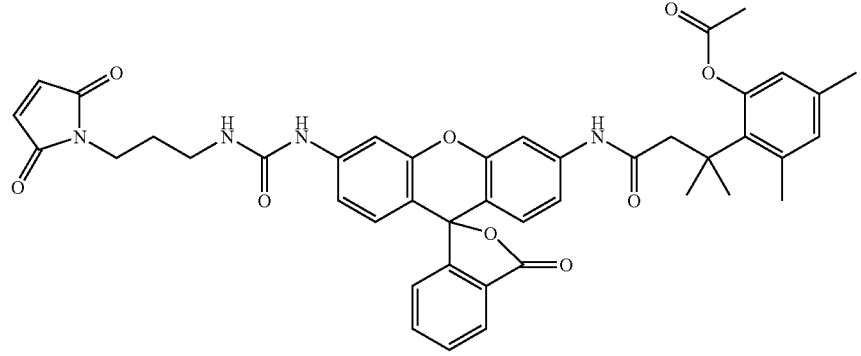

Compound B compound A (25 mg, 0.049 mmol) was dissolved in a mixture of anhydrous DMF (3 mL) and anhydrous pyridine (2 mL). To the solution was added N-ethyl-N'-(3-dimethylaminopropyl) carbodiimide (36 mg, 0.196 mmol) and 3-(2'-acetoxy-4'6'-dimethylphenyl)-3,3-dimethylpropanoic acid (56 mg, 0.196 mmol). The resulting solution was stirred at ambient temperature for 24 hours. The solvents were removed under reduced pressure and the residue was partitioned between 50 mL each of EtOAc and phthalate buffer (pH=5.0). The layers were separated and the aqueous layer extracted with EtOAc (2×50 mL). The combined organic layers were washed with saturated NH$_4$Cl solution (1×50 mL) and dried over anhydrous MgSO$_4$. Removal of the solvent under reduced pressure followed by silica gel column chromatography using 4:1 EtOAc: hexanes gave 29 mg of a pale pink solid (yield: 78%). MS, m/z=757.0 (M+H$^+$).

Preparation of Compound C:

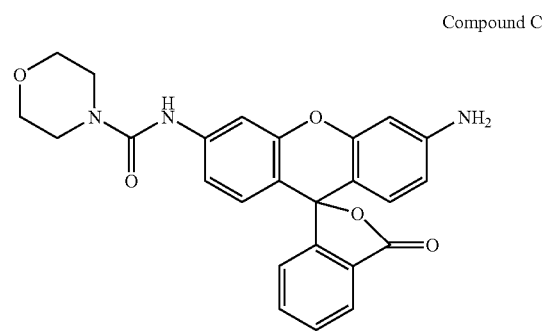

Compound C

Rhodamine 110 (200 mg, 0.545 mmol) was dissolved in anhydrous DMF (10 mL). To the DMF solution was added N,N-diisopropylethylamine (0.285 mL) and the resulting orange solution was stirred at ambient temperature for 5 minutes. 4-Morpholinecarbonyl chloride (74 mg, 0.496 mmol) was added dropwise and the resulting mixture was stirred for 48 hours at ambient temperature. The solvents were removed under reduced pressure and the residue was purified via silica gel chromatography using a 5% to 15% gradient of MeOH in CHCl$_3$. The purification gave 66 mg of a red-orange crystalline solid (yield: 30%). MS, m/z=478.1 (M+Cl$^-$).

Preparation of Compound D:

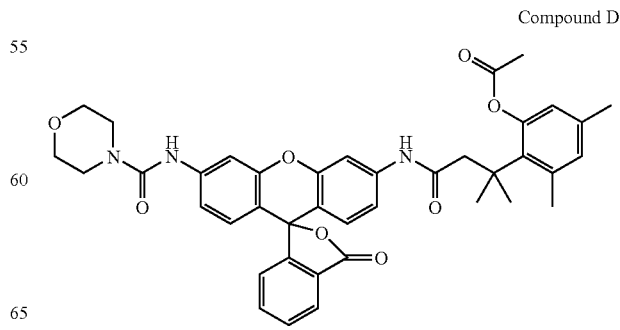

Compound D

Rhodamine 110 (628 mg, 1.71 mmol) was dissolved in anhydrous DMF (10 mL). To the DMF solution was added N,N-diisopropylethylamine (1.2 mL) and the resulting orange solution was stirred at ambient temperature for 5 minutes. 4-Morpholinecarbonyl chloride (282 mg, 0.188 mmol) was added dropwise and the resulting mixture was stirred for 48 hours at ambient temperature. The solvents were removed under reduced pressure and the residue dried on high vacuum for 24 hours. The residue was then dissolved in a mixture of anhydrous DMF (3 mL) and anhydrous pyridine (2 mL). To this solution was added N-ethyl-N'-(3-dimethylaminopropyl)carbodiimide (492 mg, 2.57 mmol) and 3-(2'-acetoxy-4'6'-dimethylphenyl)-3,3-dimethylpropanoic acid (731 mg, 2.57 mmol). The resulting solution was stirred at ambient temperature for 48 hours. The solvents were removed under reduced pressure and the residue was taken up in $CH_2Cl_2$ (200 mL). This solution was washed with 5% HCl (1×100 mL) saturated NaCl solution (1×100 mL) and dried over anhydrous $MgSO_4$. Removal of the solvent under reduced pressure followed by silica gel column chromatography using 2:1 EtOAc:hexanes gave 134 mg of a pale pink solid (yield: 11% for two steps). MS, m/z=712.1 (M+Na$^+$).

Preparation of Compound E:

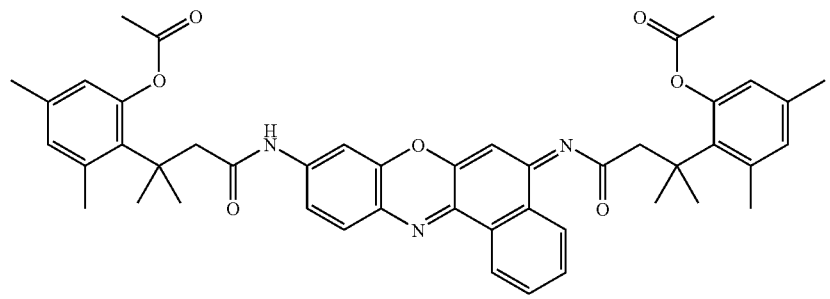

Compound E 3-(2'-Acetoxy-4'6'-dimethylphenyl)-3,3-dimethylpropanoic acid (394 mg, 1.38 mmol) was dissolved in a mixture of anhydrous DMF (2 mL) and anhydrous pyridine (2 mL). N-Ethyl-N'-(3-dimethylaminopropyl)carbodiimide (265 mg, 1.38 mmol) was added and the reaction mixture was stirred for 30 minutes at ambient temperature. Cresyl Violet 670 perchlorate (250 mg, 0.691 mmol) was added to the purple solution and the reaction was stirred at ambient temperature for 24 hours. The solvents were removed under reduced pressure and the residue was partitioned between 100 mL each of EtOAc and 5% HCl. The layers were separated and the aqueous layer extracted with EtOAc (2×100 mL). The combined organic layers were washed with $H_2O$ (1×100 mL), saturated NaCl solution (1×100 mL) and dried over anhydrous $MgSO_4$. Removal of the solvent under reduced pressure followed by silica gel column chromatography 30% EtOAc in hexanes gave 55 mg of a brown solid (yield: 11%). MS, m/z=753.9 (M$^+$).

Preparation of Protein Conjugate Using Compound B:

The A19C mutant of Ribonuclease A (4.4 mg, 0.32 μmol) in PBS (2.0 mL) was transferred to a small reaction vessel. Compound B (9.9 mg, 0.0131 mmol) in DMF (0.250 mL) was added dropwise and the reaction stirred for 3 hours at ambient temperature. Precipitate was removed by centrifugation and the solution was dialyzed against 1×PBS at ambient temperature for 24 hours. Purification of the protein conjugate using cation-exchange chromatography afforded the desired product. MS, m/z=14475 (M+H$^+$)

Activation of Compound D by Porcine Liver Esterase:

Various concentrations of Compound D were incubated with a solution of 2.5 μg/mL of Porcine Liver Esterase (PLE). To a quartz cuvette containing 1990 μL of 1×PBS was added 5 μL of a stock solution in DMSO followed by 5 μL of 1.0 mg/mL PLE. The increase in fluorescence was measured using 496 nm as the excitation wavelength and monitoring emission at 520 nm using a fluorometer (Photon Technologies International). A calibration curve was prepared using compound C. The initial velocities values were plotted on a double reciprocal plot giving a $k_{cat}/K_m$ value of $7\times10^5$ $M^{-1}$ $s^{-1}$.

Activation of Compound E by Porcine Liver Esterase:

Various concentrations of Compound E were incubated with a solution of 2.5 μg/mL of Porcine Liver Esterase (PLE). To a quartz cuvette containing 1990 μL of 1×PBS was added 5 μL of a stock solution in DMSO followed by 5 μL of 1.0 mg/mL PLE. The increase in fluorescence was measured using 591 nm as the excitation wavelength and monitoring emission at 628 nm using a fluorometer (Photon Technologies International). A calibration curve was prepared using compound Cresyl Violet 640 Perchlorate. The initial velocities values were plotted on a double reciprocal plot giving a $k_{cat}/K_m$ value of $2\times10^5$ $M^{-1}s^{-1}$.

The pyridine used was dried by storage for 24 h over activated Linde 4A molecular sieves under Ar(g). Anhydrous DMF was obtained from a CYCLE-TAINER solvent delivery system (J. T. Baker; Phillipsburg, N.J.). EDCI was from Novabiochem. Rhodamine 110 was from Aldrich Chemical (Milwaukee, Wis.). Silica gel 60 (230-400 mesh) for flash chromatography was from Silicycle (Quebec City, Quebec, Canada).

$^1$H NMR and $^{13}$C NMR spectra were obtained with a BrukerAC+300 spectrometer at the University of Wisconsin-Madison Chemistry Instrument Center. All kinetic evaluations were performed in phosphate-buffered saline (PBS, pH 7.3), which contained (in 1 L) KCl (0.2 g), $KH_2PO_4$ (0.2 g), NaCl (8.0 g), and $Na_2HPO_4.7H_2O$ (2.16 g). Pig liver esterase (PLE; product number E2884) was obtained from Sigma Chemical (St. Louis, Mo.) as a suspension in 3.2 M ammonium sulfate buffer, and was diluted to appropriate concentrations in PBS before use. Stock solutions of pro-fluorophore C were prepared in DMSO and added to PBS for the kinetic experiments such that DMSO concentrations never exceeded 1% (v/v). Fluorometric measurements were made using fluorescence grade quartz or glass cuvettes from Starna Cells (Atascadero, Calif.) and a QuantaMaster1 photon-counting spectrofluorometer from Photon Technology International (South Brunswick, N.J.) equipped with sample stirring.

Esterase Assay Using Urea-Containing Group

In another embodiment of the invention, an enzyme such as esterase is used to convert a latent fluorescent compound containing a blocking group, for example, a trimethyl-lock containing compound, and a urea-containing group into a highly fluorescent compound. One example of this embodiment is shown in Scheme XIII. The reactions were analogous to those described above. The molecule shown in Scheme XII does not activate in water, but shows rapid activation by pig liver esterase. Using pig liver esterase, the $k_{cat}/K_M$ was $7\times10^5$ $M^{-1}s^{-1}$.

Scheme XIII

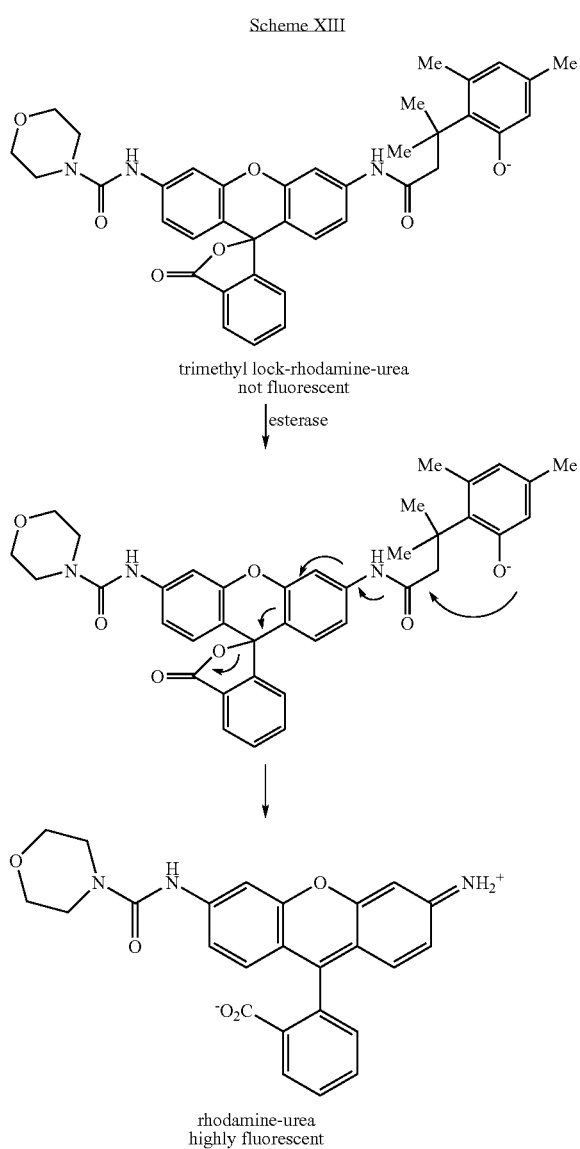

trimethyl lock-rhodamine-urea
not fluorescent

↓ esterase rhodamine-urea
highly fluorescent

Protein Systems

In order to study the routing of a ribonuclease such as RNase A to the cytosol, a means to view only the molecules that enter the cytosol is required. The cytosolic entry point cannot be determined by microscopy using a fluorescent ribonuclease because the background from the fluorescent ribonuclease bound to the cell surface or localized in endosomes is too high. A ribonuclease attached to a latent fluorescent molecule, a small molecule that is not fluorescent until it enters the cytosol provides the desired viewing means. The ribonucleases or other molecules studied can be attached to the latent fluorescent molecule at any convenient point, including a urea group, or using other appropriate linkages known to one of ordinary skill in the art without undue experimentation.

Phosphatase Assay

The latent fluorescent compounds can be used to detect phosphatases. This assay uses blocking group(s) that contain $PO_3^{2-}$ which reacts with phosphatases to release the blocking group(s) and form a fluorescent molecule.

Azide Assay

Azides ($N^{3-}$) are components of explosives. Currently, there is no simple method available to detect azides. Using the methods and compositions of the current invention, azides are used as triggers to release blocking groups from a latent fluorescent compound.

These methods and compositions provide a method to detect azides and can be used in baggage screening, for example. For use in baggage screening, a swab containing the latent fluorescent compound can be wiped over a piece of baggage. If the swab exhibits fluorescence, azides are present.

In particular, one or more blocking groups containing the group diphenylphosphine (—PPh$_2$) are attached to a fluorescent molecule, forming a latent fluorescent molecule. When exposed to azides, the azide reacts with the —PPh$_2$ group and releases the blocking group, forming the fluorescent molecule. As an alternative to forming a fluorescent molecule, the azide may release a highly colored compound that can be detected. Specific examples of fluorescent molecules that can be used to detect azides follow. In the examples following, an organic azide is used

which is formed, for example, by reaction of an inorganic azide (Pb(N$_3$)$_2$, for example) with iodoacetic acid or other suitable group, as known in the art. R is any suitable group, as known in the art, for example a C1-C6 alkyl group.

Scheme XIV

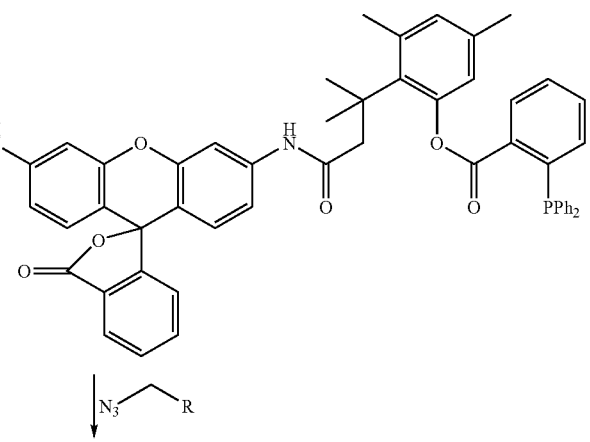

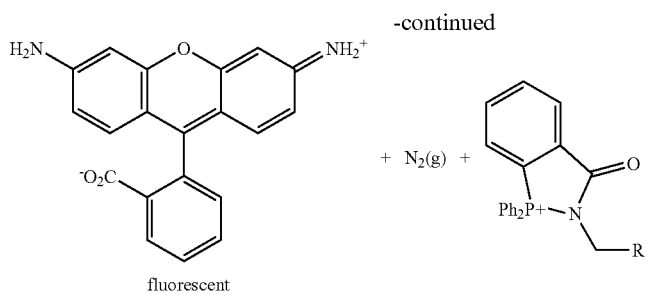

fluorescent

Scheme XV

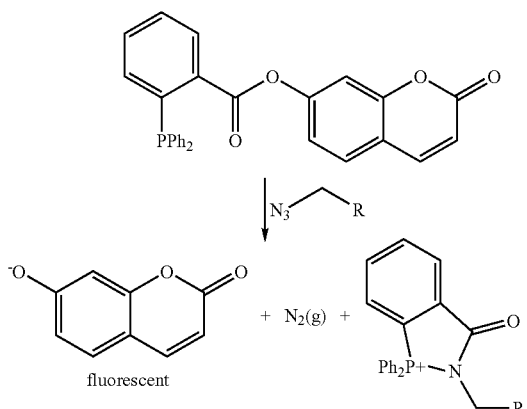

fluorescent

Scheme XVI

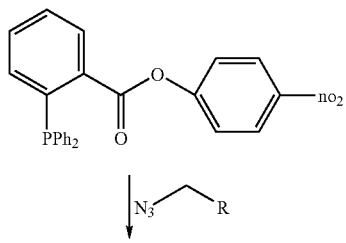

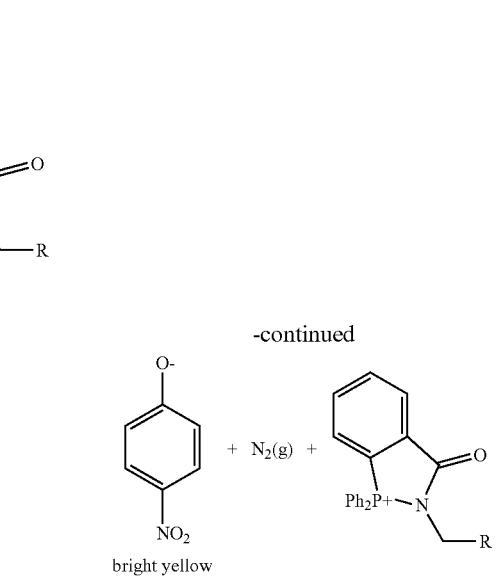

bright yellow

Attachment of Electrophilic Group to Latent Fluorescent Molecule

In this example, an electrophilic group is attached to a latent fluorescent molecule which contains a trimethyl lock. One method of synthesis is shown in Scheme XVII. Rhodamine 110 is reacted with a trimethyl lock-containing group and an electrophilic group to attach both the trimethyl lock and the electrophilic group to the rhodamine backbone. The compound is now a latent fluorescent molecule. The synthetic conditions are standard and known in the art. The trimethyl lock-containing group can be cleaved as described above to provide a fluorescent molecule. The electrophilic group can be used to covalently attach biomolecules, such as peptides, proteins or amino acids, as known in the art.

Scheme XVII

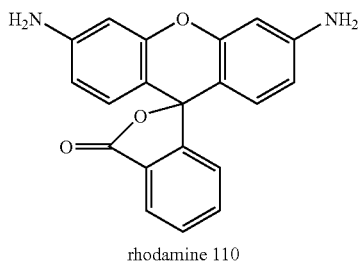

rhodamine 110

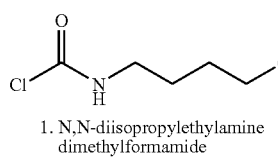

1. N,N-diisopropylethylamine
   dimethylformamide

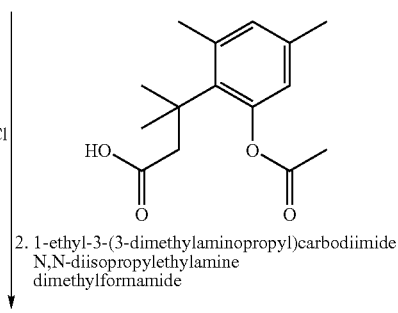

2. 1-ethyl-3-(3-dimethylaminopropyl)carbodiimide
   N,N-diisopropylethylamine
   dimethylformamide -continued

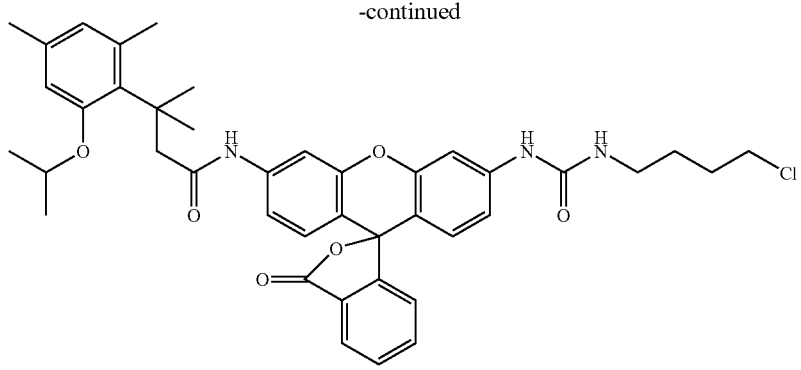

Although the description herein contains many specificities, these should not be construed as limiting the scope of the invention, but as merely providing illustrations of some of the preferred embodiments of the invention. For example, fluorescent molecules, triggers and blocking groups other than those specifically exemplified herein may be used, as known to one of ordinary skill in the art without undue experimentation. Chemical synthesis methods to attach blocking groups and urea-containing groups to fluorescent molecules are known to one of ordinary skill in the art. Thus, the scope of the invention should be determined by the appended claims and their legal equivalents, rather than by the examples given.

When a group of substituents is disclosed herein, it is understood that all individual members of those groups and all subgroups, including any isomers and enantiomers of the group members, and classes of compounds that can be formed using the substituents are disclosed separately. When a compound is claimed, it should be understood that compounds known in the art including the compounds disclosed in the references disclosed herein are not intended to be included. In particular, it should be understood that any compound for which an enabling disclosure is provided in any reference cited in this specification is to be excluded from the claims herein if appropriate. When a Markush group or other grouping is used herein, all individual members of the group and all combinations and subcombinations possible of the group are intended to be individually included in the disclosure. Unless otherwise indicated, when a compound is described and/or claimed herein, it is intended that any ionic forms of that compound, particularly carboxylate anions and protonated forms of the compound as well as any salts thereof are included in the disclosure. Counter anions for salts include among others halides, carboxylates, carboxylate derivatives, halogenated carboxylates, sulfates and phosphates. Counter cations include among others alkaki metal cations, alkaline earth cations, and ammonium cations.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomer and enantiomer of the compound described individually or in any combination. One of ordinary skill in the art will appreciate that methods, device elements, starting materials, synthetic methods, and detection methods other than those specifically exemplified can be employed in the practice of the invention without resort to undue experimentation. All art-known functional equivalents, of any such methods, starting materials, synthetic methods, and detection methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In general the terms and phrases used herein have their art-recognized meaning, which can be found by reference to standard texts, journal references and contexts known to those skilled in the art. The specific definitions are provided to clarify their specific use in the context of the invention.

All patents and publications mentioned in the specification are indicative of the levels of skill of those skilled in the art to which the invention pertains.

One skilled in the art would readily appreciate that the present invention is well adapted to carry out the objects and obtain the ends and advantages mentioned, as well as those inherent therein. The compounds and methods and accessory methods described herein as presently representative of preferred embodiments are exemplary and are not intended as limitations on the scope of the invention. Changes therein and other uses will occur to those skilled in the art, which are encompassed within the spirit of the invention, are defined by the scope of the claims.

Although the description herein contains many specificities, these should not be construed as limiting the scope of the invention, but as merely providing illustrations of some of the embodiments of the invention. Thus, additional embodiments are within the scope of the invention and within the following claims. All references cited herein are hereby incorporated by reference to the extent that there is no inconsistency with the disclosure of this specification. Some references provided herein are incorporated by reference herein to provide details concerning additional starting materials, additional methods of synthesis, additional methods of analysis and additional uses of the invention.

REFERENCES

S. K. Saxena, J. Biol. Chem. 266:21208-21214, 1991
M. C. Haigis et al., J. Cell Sci. 116:313-324, 2003
G. Zlokarnik et al., Science 279:84-88, 1998
J. M. Goldberg et al., Biochemistry 37:2546-2555, 1998
S. Milstein et al., Proc. Natl. Acad. Sci. USA 67:1143-1147, 1970
J. M. Karle et al., J. Am. Chem. Soc. 94:9182-9189, 1972
S. Milstein et al., J. Am. Chem. Soc. 94:9158-9165, 1972
D. Shan et al., J. Pharm. Sci. 86:765-767, 1997
R. B. Greenwald et al., J. Med. Chem. 43:475-487, 2000
M. M. Fickling et al., J. Am. Chem. Soc. 81:4226-4230, 1959
T. Karstens et al., J. Phys. Chem. 84:1871-1872, 1980
S. M. Mikulski et al., J. Clin. Oncol. 20:274-281, 2002
D. Hall et al., Biochim. Biophys. Acta 1649:127-139, 2003
P. O. Seglen et al., Eur. J. Biochem. 95:215-225, 1979
B. Valeur, Molecular Fluorescence: Principles and Applications, Wiley-VCH, Weinheim, Germany, 2002
J. R. Lakowicz, Principles of Fluorescence Spectroscopy, $2^{nd}$ Ed., Plenum Publishing, New York, 1999
W. T. Mason, Fluorescent and Luminescent Probes for Biological Activity, $2^{nd}$ Ed., Academic Press, San Diego, Calif., 1999
J. Zhang et al., Nat. Rev. Mol. Cell. Biol. 3:906-918, 2002
G. Zlokarnik et al., Science 279:84-88, 1998
R. T. Borchardt et al., J. Am. Chem. Soc. 94:9166-9174, 1972
J. M. Karle et al., J. Am. Chem. Soc. 94:9182-9189, 1972
C. Danforth et al., J. Am. Chem. Soc. 98:4275-4281, 1976
B. Testa et al., Hydrolysis in Drug and Prodrug Metabolism, Verlag Helvetica Chimica Acta, Zurich, Switzerland, 2003
K. L. Amsberry et al., Pharm. Res. 8:323-330, 1991
K. L. Amsberry et al., Pharm. Res. 8:455-461, 1991
M. Dillon et al., Bioorg. Med. Chem. Lett. 6:1653-1656, 1996
M. G. Nicolaou et al., J. Org. Chem. 61:8636-8641, 1996
G. M. Pauletti et al., Pharm. Res. 14:11-17, 1997
R. B. Greenwald et al., J. Med. Chem. 43:475-487, 2000
K. Achilles, Arch. Pharm. Med. Chem. 334:209-215, 2001
B. Rotman et al., Proc. Natl. Acad. Sci. USA 55:134-141, 1966
J. M. Goldberg et al., Biochemistry 37:2546-2555, 1998
S. P. Leytus et al., Biochem. J. 209:299-307, 1983

We claim
1. A latent fluorescent compound comprising the following structure:

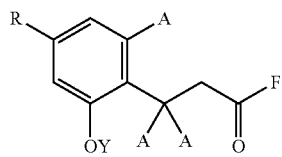

wherein F is a fluorophore having the structure:

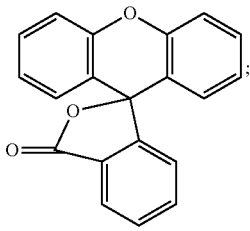

each A is independently a C1-C12 straight chain or branched alkyl group or alkoxy group;
R is a C1-C12 straight chain or branched alkyl group or alkoxy group;
Y is selected from hydrogen, $—PO_3(R^1)_2$, straight-chain, branched or cyclic C1-C20 alkyl groups in which one or more of the carbon atoms are optionally substituted with non-hydrogen substituents and wherein one or more C, CH, or $CH_2$ moieties can be replaced with an O atom, a nitrogen atom, an $NR^1$ group, or a S atom; straight-chain, branched or cyclic C1-C20 alkenyl group which contains one or more double bonds in which one or more of the carbon atoms are optionally substituted with non-hydrogen substituents and wherein one or more C, CH, or $CH_2$ moieties can be replaced with an O atom, a —CO— group, a —OCO— group, a nitrogen atom, an $NR^1$ group, or a S atom; straight-chain, branched or cyclic C1-C20 alkynyl group which contains one or more triple bonds in which one or more of the carbon atoms are optionally substituted with non-hydrogen substituents and wherein one or more C, CH, or $CH_2$ moieties can be replaced with an O atom, a —CO— group, a —OCO— group, a nitrogen atom, an $NR^1$ group, or a S atom; and an optionally substituted aromatic or non-aromatic ring structure, wherein: R can optionally be substituted with one or more substituent groups selected from halogens; nitro groups; cyano groups; isocyano groups; thiocyano groups; isothiocyano groups; azide groups; $—SO_2$ groups; $—OSO_3H$ groups; one or more optionally substituted straight-chain, branched or cyclic alkyl, alkenyl or alkynyl groups; $OR^1$; $—CO—OR^1$; $—O—CO—R^1$; $—N(R^1)_2$; $—CO—N(R^1)_2$; $—NR^1—CO—OR^1$; $—SR^1$; $—SOR^1$; $—SO_2—R^1$; $—SO_3R^1$; $—SO_2N(R^1)_2$; $—P(R^1)_2$; $—OPO_3(R_1)_2$; and $—Si(R^1)_3$ wherein each $R^1$, independent of other $R^1$ in the substituent group can be a hydrogen, an optionally substituted straight-chain, branched or cyclic alkyl, alkenyl or alkynyl group wherein one or more C, CH or $CH_2$ groups therein can be replaced with an O atom, N atom, S atom or —NH group; an optionally substituted aromatic group, two or more $R^1$ groups can be linked together to form a ring which may contain one or more of the same or different heteroatoms; and $R^1$ can in turn be optionally substituted with one or more groups selected from the group consisting of halogens, nitro groups; cyano groups; isocyano groups; thiocyano groups; isothiocyano groups; azide groups; $—SO_2$ groups; $—OSO_3H$ groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups.

2. The compound of claim 1, wherein each A is independently a C1-C5 alkyl or alkoxy group.

3. The compound of claim 1, wherein each A is a methyl group.

4. The compound of claim 1 having the structure:

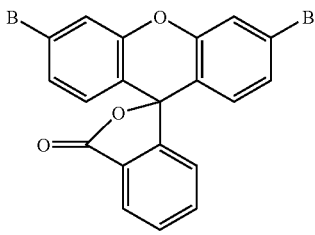

wherein the B's may be the same or different and B is a blocking group having the structure:

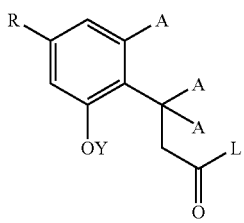

where L is a direct bond, —NH—, or —O—;
Y is selected from the group consisting of:
hydrogen, —PO$_3$(R$^1$)$_2$,
straight-chain, branched or cyclic C1-C20 alkyl groups in which one or more of the carbon atoms are optionally substituted with non-hydrogen substituents and wherein one or more C, CH, or CH$_2$ moieties can be replaced with an O atom, a nitrogen atom, an NR$^1$ group, or a S atom;
straight-chain, branched or cyclic C1-C20 alkenyl group which contains one or more double bonds in which one or more of the carbon atoms are optionally substituted with non-hydrogen substituents and wherein one or more C, CH, or CH$_2$ moieties can be replaced with an O atom, a —CO— group, a —OCO— group, a nitrogen atom, an NR$^1$ group, or a S atom;
straight-chain, branched or cyclic C1-C20 alkynyl group which contains one or more triple bonds in which one or more of the carbon atoms are optionally substituted with non-hydrogen substituents and wherein one or more C, CH, or CH$_2$ moieties can be replaced with an O atom, a —CO— group, a —OCO— group, a nitrogen atom, an NR$^1$ group, or a S atom; and
an optionally substituted aromatic or non-aromatic ring structure, wherein:
R can optionally be substituted with one or more substituent groups selected from halogens; nitro groups; cyano groups; isocyano groups; thiocyano groups; isothiocyano groups; azide groups; —SO$_2$ groups; —OSO$_3$H groups; one or more optionally substituted straight-chain, branched or cyclic alkyl, alkenyl or alkynyl groups; OR$^1$; —CO—OR$^1$; —O—CO—R$^1$; —N(R$^1$)$_2$; —CO—N(R$^1$)$_2$; —NR$^1$—CO—OR$^1$; —SR$^1$; —SOR$^1$; —SO$_2$—R$^1$; —SO$_3$R$^1$; —SO$_2$N(R$^1$)$_2$; —P(R$^1$)$_2$; —OPO$_3$(R$_1$)$_2$; and —Si(R$^1$)$_3$ wherein each R$^1$, independent of other R$^1$ in the substituent group can be a hydrogen, an optionally substituted straight-chain, branched or cyclic alkyl, alkenyl or alkynyl group wherein one or more C, CH or CH$_2$ groups therein can be replaced with an O atom, N atom, S atom or —NH group; an optionally substituted aromatic group, two or more R$^1$ groups can be linked together to form a ring which may contain one or more of the same or different heteroatoms; and
R$^1$ can in turn be optionally substituted with one or more groups selected from the group consisting of halogens, nitro groups; cyano groups; isocyano groups; thiocyano groups; isothiocyano groups; azide groups; —SO$_2$ groups; —OSO$_3$H groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups;
each A is independently a C1-C12 straight chain or branched alkyl group or alkoxy group; and
R is a C1-C12 straight chain or branched alkyl group or alkoxy group.

5. The compound of claim 1, having the following structure:

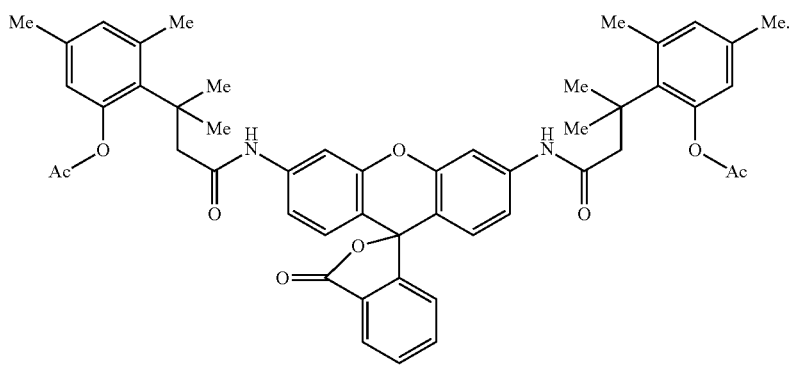

6. A latent fluorescent compound having the structure:

(B)$_a$—F where a is 1 or 2;

F is a fluorescent molecule having the structure

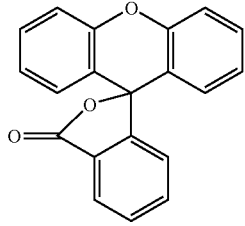

wherein each B is a blocking group having the structure:

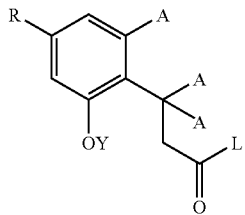

where L is either a direct bond, —NH—, or —O—;

Y is selected from the group consisting of:

hydrogen, —PO$_3$(R$^1$)$_2$, straight-chain, branched or cyclic C1-C20 alkyl groups in which one or more of the carbon atoms are optionally substituted with non-hydrogen substituents and wherein one or more C, CH, or CH$_2$ moieties can be replaced with an O atom, a nitrogen atom, an NR$^1$ group, or a S atom;

straight-chain, branched or cyclic C1-C20 alkenyl group which contains one or more double bonds in which one or more of the carbon atoms are optionally substituted with non-hydrogen substituents and wherein one or more C, CH, or CH$_2$ moieties can be replaced with an O atom, a —CO— group, a —OCO— group, a nitrogen atom, an NR$^1$ group, or a S atom;

straight-chain, branched or cyclic C1-C20 alkynyl group which contains one or more triple bonds in which one or more of the carbon atoms are optionally substituted with non-hydrogen substituents and wherein one or more C, CH, or CH$_2$ moieties can be replaced with an O atom, a —CO— group, a —OCO— group, a nitrogen atom, an NR$^1$ group, or a S atom; and an optionally substituted aromatic or non-aromatic ring structure, wherein:

R can optionally be substituted with one or more substituent groups selected from halogens; nitro groups; cyano groups; isocyano groups; thiocyano groups; isothiocyano groups; azide groups; —SO$_2$ groups; —OSO$_3$H groups; one or more optionally substituted straight-chain, branched or cyclic alkyl, alkenyl or alkynyl groups; OR$^1$; —CO—OR$^1$; —O—CO—R$^1$; —N(R$^1$)$_2$; —CO—N(R$^1$)$_2$; —NR$^1$—CO—OR$^1$; —SR$^1$; —SOR$^1$; —SO$_2$—R$^1$; —SO$_3$R$^1$; —SO$_2$N(R$^1$)$_2$; —P(R$^1$)$_2$; —OPO$_3$(R$_1$)$_2$; and —Si(R$^1$)$_3$ wherein each R$^1$, independent of other R$^1$ in the substituent group can be a hydrogen, an optionally substituted straight-chain, branched or cyclic alkyl, alkenyl or alkynyl group wherein one or more C, CH or CH$_2$ groups therein can be replaced with an O atom, N atom, S atom or —NH group; an optionally substituted aromatic group, two or more R$^1$ groups can be linked together to form a ring which may contain one or more of the same or different heteroatoms; and R$^1$ can in turn be optionally substituted with one or more groups selected from the group consisting of halogens, nitro groups; cyano groups; isocyano groups; thiocyano groups; isothiocyano groups; azide groups; —SO$_2$ groups; —OSO$_3$H groups; straight-chain, branched or cyclic alkyl, alkenyl or alkynyl groups; halogenated alkyl groups; hydroxyl groups; alkoxy groups; carboxylic acid and carboxylic ester groups; amine groups; carbamate groups, thiol groups, thioether and thioester groups; sulfoxide groups, sulfone groups; sulfide groups; sulfate and sulfate ester groups; sulfonate and sulfonate ester groups; sulfonamide groups, sulfonate ester groups; phosphine groups; phosphate and phosphate ester groups; phosphonate and phosphonate ester groups; and alkyl-substituted silyl groups;

each A is independently a C1-C12 straight chain or branched alkyl group or alkoxy group;

R is a C1-C12 straight chain or branched alkyl group or alkoxy group.

* * * * *